(12) United States Patent
Sarnow et al.

(10) Patent No.: US 11,064,971 B2
(45) Date of Patent: Jul. 20, 2021

(54) NON-INVASIVE DETERMINATION OF MUSCLE TISSUE QUALITY AND INTRAMUSCULAR FAT

(71) Applicant: MuscleSound, LLC, Glendale, CO (US)

(72) Inventors: Pierre Sarnow, Littleton, CO (US); Stephen S. Kurtz, Englewood, CO (US); Andrew D. Jackson, Denver, CO (US); Wayne Phillips, Gilbert, AZ (US)

(73) Assignee: MuscleSound, Inc., Glendale, CO (US)

( * ) Notice: Subject to any disclaimer, the term of this patent is extended or adjusted under 35 U.S.C. 154(b) by 478 days.

(21) Appl. No.: 15/818,999

(22) Filed: Nov. 21, 2017

(65) Prior Publication Data

US 2018/0146947 A1    May 31, 2018

Related U.S. Application Data

(60) Provisional application No. 62/428,300, filed on Nov. 30, 2016.

(51) Int. Cl.
*A61B 8/08* (2006.01)
*A61B 8/00* (2006.01)

(52) U.S. Cl.
CPC .......... *A61B 8/0866* (2013.01); *A61B 8/0858* (2013.01); *A61B 8/461* (2013.01);
(Continued)

(58) Field of Classification Search
CPC ... A61B 8/0866; A61B 8/0858; A61B 8/5223; A61B 8/5207; A61B 8/461; A61B 8/4483
See application file for complete search history.

(56) References Cited

U.S. PATENT DOCUMENTS

| | | | |
|---|---|---|---|
| 4,831,527 A | 5/1989 | Clark | |
| 4,876,733 A * | 10/1989 | Lavin | G06T 5/20 |
| | | | 382/205 |

(Continued)

FOREIGN PATENT DOCUMENTS

WO    WO 14/115056    7/2014

OTHER PUBLICATIONS

Costill, et al., "Muscle glycogen utilizaation during prolonged exercise on successive days," *Journal of Applied Physiology*, 1971, vol. 31, No. 6, pp. 834-838.
(Continued)

*Primary Examiner* — Hien N Nguyen
(74) *Attorney, Agent, or Firm* — Brownstein Hyatt Farber Schreck, LLP

(57) ABSTRACT

Provided is a non-invasive system and method of determining muscle tissue quality based on image processing. The non-invasive system and method includes determining muscle intramuscular fat content. The methods includes receiving at least one ultrasound scan image of at least a portion of a skin layer as disposed above one or more additional tissue layers, the skin layer defining a horizontal axis and the image provided by a plurality of pixels. The method continues by blurring the pixels of the image and thresholding the pixels of the image to provide an image having a plurality of structural elements of different sizes and gray scale. The method continues with morphing the structural elements of the image to remove small structural elements and connect large structural elements. With this resulting image, the method distinguishes muscle tissue from remaining elements. A ratio of black to white elements is evaluated to determine the muscle tissue quality or intramuscular fat content. Associated apparatuses and computer program products are also disclosed.

19 Claims, 14 Drawing Sheets

(52) U.S. Cl.
CPC .......... *A61B 8/5207* (2013.01); *A61B 8/5223* (2013.01); *A61B 8/4483* (2013.01)

(56) References Cited

U.S. PATENT DOCUMENTS

| | | | |
|---|---|---|---|
| 5,208,747 A * | 5/1993 | Wilson | A22B 5/007 600/443 |
| 5,670,135 A | 9/1997 | Schroder | |
| 5,941,825 A | 8/1999 | Lang et al. | |
| 6,542,250 B1 | 2/2003 | Weber et al. | |
| 6,656,121 B2 | 12/2003 | Jeong et al. | |
| 6,705,994 B2 | 3/2004 | Vortman et al. | |
| 7,658,714 B2 | 2/2010 | Leibig et al. | |
| 7,664,298 B2 | 2/2010 | Lang et al. | |
| 7,683,617 B2 | 3/2010 | Van Zijl et al. | |
| 7,918,794 B2 | 4/2011 | Pineau et al. | |
| 8,315,179 B2 | 3/2012 | Wilson et al. | |
| 8,512,247 B2 * | 8/2013 | Hill | A61B 8/5223 600/365 |
| 8,517,942 B2 | 8/2013 | Hill | |
| 8,562,529 B2 | 10/2013 | Hill | |
| 8,715,187 B2 | 5/2014 | Davis et al. | |
| 8,811,745 B2 | 8/2014 | Farsiu et al. | |
| 9,364,179 B2 | 6/2016 | Hill | |
| 9,579,079 B2 | 2/2017 | Jeanne et al. | |
| 9,642,593 B2 | 5/2017 | Sarnow et al. | |
| 2003/0018257 A1 | 1/2003 | Hsu et al. | |
| 2004/0125987 A1 | 7/2004 | Haagensen | |
| 2004/0131227 A1 | 7/2004 | Bravomalo | |
| 2006/0184024 A1 | 8/2006 | Da Silva et al. | |
| 2007/0016061 A1 | 1/2007 | Da Silva et al. | |
| 2009/0264756 A1 | 10/2009 | Da Silva et al. | |
| 2009/0270728 A1 | 10/2009 | Da Silva et al. | |
| 2009/0274340 A1 * | 11/2009 | Wilson | G01N 33/12 382/110 |
| 2010/0036246 A1 | 2/2010 | Kushculey et al. | |
| 2012/0116223 A1 | 5/2012 | Da Silva et al. | |
| 2012/0165703 A1 | 6/2012 | Bottum | |
| 2012/0254749 A1 | 10/2012 | Downs, III et al. | |
| 2013/0123629 A1 | 5/2013 | Rosenberg et al. | |
| 2015/0374343 A1 | 12/2015 | Shan et al. | |
| 2016/0110875 A1 * | 4/2016 | Sugiyama | A61B 8/0825 382/131 |
| 2016/0249887 A1 | 9/2016 | Hill et al. | |
| 2017/0035352 A1 | 2/2017 | Appleby | |
| 2017/0046837 A1 | 2/2017 | Leinhard | |
| 2017/0209090 A1 | 7/2017 | Sarnow et al. | |
| 2018/0132817 A1 | 5/2018 | Sarnow et al. | |
| 2018/0214118 A1 | 8/2018 | Sarnow et al. | |
| 2018/0249946 A1 | 9/2018 | Sarnow et al. | |

OTHER PUBLICATIONS

Gabriel et al., "Ultrasound of the abdomen in endurance athletes," *Eur J Appl Physiol*, 1996, vol. 73, pp. 191-193.

Jackson et al., "Practical Assessment of Body Composition," *Physicians Sports Medicine*, 1985, vol. 13, pp. 76-90.

Kadah et al., "Classification Algorithms for Quantitative Tissue Characterization of Diffuse Liver Disease from Ultrasound Imaages," *IEEE Transactions on Medical Imaging*, 1996, vol. 15, No. 4, pp. 466-478.

Koda et al., "Sonographic subcutaneous and visceral fat indices represent the distribution of body fat volume," *Abdominal Imaging*, 2007, vol. 32, pp. 387-392.

Leahy et al., "Ultrasound Measurement of Subcutaneous Adipose Tissue Thickness Accurately Predicts Total and Segmental Body Fat of Young Adults," Ultrasound in Medicine and Biology, 2012, vol. 38, No. 1, pp. 28-34.

Nguyen et al., "Contrast-Enhanced Ultrasonography in Patients with Glycogen Storage Disease Type Ia and Adenomas," *Journal of Ultrasound Medicine*, 2009, vol. 28, pp. 497-505.

Price et al., "Effect of muscle glycogen content on exercise-induced changes in muscle T2 times," *Muscle Glycogen, Exercise, and T2 Times*, 1998, pp. 1178-1184.

Steensberg et al., "Muscle glycogen content and glucose uptake during exercise in humans: influence of prior exercise and dietary manipulation," *Journal of Physiology*, vol. 541.1, 2002, pp. 273-281.

Wagner, "Ultrasound as a Tool to Assess Body Fat," *Journal of Obesity*, vol. 2013, Article ID 280713, 9 pages.

Elamaran et al., "A Case Study of Impulse Noise Reduction Using Morphological Image Processing with Structuring Elements," *Asian Journal of Scientific Research*, vol. 8, No. 3, 2015, pp. 291-303.

Fisher et al., "Spatial Filters—Gaussian Smoothing," https://homepages.inf.ed.ac.uk/rbf/HIPR2/gsmooth.htm, Apr. 24, 2020, 9 pages.

MathWorks Announces Release 2014a of the MATLAB and Simulink Product Families, https://www.mathworks.com/company/newsroom/mathworks-announces-release-2014a-of-the-matlab-and-simulink-product-families.html, Mar. 7, 2014, 6 pages.

Zhou et al., "Automatic measurement of pennation angle and fascicle length of gastrocnemius muscles ultrasound imaging," *Ultrasonics*, vol. 57, 2015, pp. 72-83.

Definition of "doubling," https://www.thefreedictionary.com/doubling, retrieved on Jan. 28, 2021.

Salvi, "Architectural Analysis of Musculoskeletal Ultrasound Images," Politecnico di Torino, Dec. 2014, 61 pages.

The University of Auckland, "Gaussian Filtering," May 25, 2010, 15 pages.

* cited by examiner

NON-INVASIVE DETERMINATION OF MUSCLE TISSUE QUALITY AND INTRAMUSCULAR FAT

CROSS-REFERENCE TO RELATED APPLICATION

This application claims the benefit under 35 U.S.C. § 119(e) to U.S. Provisional Patent Application No. 62/248,300, filed Nov. 30, 2016, and entitled "Non-Invasive Determination of Muscle Tissue Quality and Intramuscular Fat," the contents of which are incorporated by reference as if fully disclosed herein.

FIELD

The described embodiments relate generally to the field of fitness and healthcare, and more specifically to non-invasive determination of muscle tissue quality and/or intramuscular fat.

BACKGROUND

The human body is composed of many types of tissues, not the least of which are bone, muscle, nervous, connective, circulatory and of course muscle tissue. For most people, the quality of certain types of tissues within the body, such as skeletal muscle tissue, can be altered by choices in diet and exercise, as well as, by injury, disease pathways and the aging process.

Determination of the quality of muscle tissue may be useful for a variety of reasons. For example, professional athletes may use such measurements to adjust a training regimen, such as to maximize muscle composition for strength, power, mobility, fitness, appearance, and so on. By way of another example, medical professionals may use such quality measurements for evaluating a patient's muscles as an indicator of the patients overall health and mobility. In yet another example, fitness enthusiasts may use such quality measurements to ensure that an injured muscle has been fully healed prior to rejoining full activity.

In another example, quality measurements can provide insight into the loss of muscle with aging, known as Sarcopenia, which has been described as " . . . the single most frequent cause of late life disability." From this perspective, the importance of studying the quality of muscle was emphasized by a panel of experts during which it was concluded that there is a need for "more comprehensive evaluations of muscle quality using noninvasive methods."

Characterizations of muscle strength, power and mass are related not only to sports performance and physical function generally, but also to quality of life and a range of health issues. Strength, power and muscle mass all decline with age, though not at the same rate. Power is lost much faster than strength, and strength is lost up to three times as much as muscle mass.

In addition to muscle quality, the determination of amount and location of intramuscular fat in a patient is useful in identifying and monitoring potential health conditions associated with obesity, dyslipidemia, glucose intolerance and cardiovascular disease, for example. Either or both values, muscle tissue quality and intramuscular fat, present useful criteria for an individual's physical condition and state of health.

At present, there are few effective ways to determine the quality of a muscle or the amount and location of intramuscular fat, particularly ways to non-invasively determine the quality of a muscle and amount and location of intramuscular fat.

SUMMARY

The present disclosure relates to non-invasive determination of muscle tissue quality. At least one ultrasound scan image of at least a portion of a skin layer as disposed above one or more additional tissue layers is received. The pixels of the ultrasound scan image are blurred (e.g. noise is introduced into the pixels). The pixels of the ultrasound scan image are thresholded to provide an image having a plurality of elements set as black or white. The black pixels correspond to contractile muscle fiber, and white pixels to non-contractile tissue (fat and connective tissue). Muscle tissue is distinguished from remaining structural elements. The muscle tissue quality is determined as a ratio of black elements to white elements.

The present disclosure relates to non-invasive determination of intramuscular fat. At least one ultrasound scan image of at least a portion of a skin layer as disposed above one or more additional tissue layers is received. The pixels of the ultrasound scan image are blurred, forming blurred pixels. The pixels of the ultrasound scan image are thresholded to provide an image having a plurality of elements set as black or white. The black pixels correspond to contractile muscle fiber. The white pixels are further differentiated to fat tissue and other connective tissue. The intramuscular fat for a muscle is then determined by taking the total area of black pixels and subtracting from it the total number of pixels that correspond to fat. The resultant number is divided by the total area of black pixels to provide a intramuscular fat percent.

In various implementations, a non-invasive method of determining human muscle tissue quality includes receiving at least one ultrasound scan image of at least a portion of a skin layer as disposed above one or more additional tissue layers, the skin layer defining a horizontal axis and the ultrasound scan image provided by a plurality of pixels; blurring the pixels of the ultrasound scan image; thresholding the blurred pixels of the ultrasound scan image to provide an image having a plurality of black or white elements; distinguishing muscle tissue from remaining structural elements; and determining the muscle tissue quality.

In some examples, one or more systems or apparatuses may perform this method. In various examples, the method is repeated over time upon additional ultrasound scan images to evaluate the quality of a muscle tissue over time.

In numerous examples, distinguishing the muscle tissue further includes evaluating at least a subset of the remaining structural elements. In some cases of such examples, evaluating at least a subset of the remaining structural elements includes determining, for each element, one or more characteristics selected from a group including: area, center of mass, and horizontal length based on gray scale. In various cases of such examples, the muscle tissue is distinguished to be a tissue layer between a topmost generally horizontal white band that is generally horizontally continuous across the binary image and a bottommost generally horizontal white band that is generally horizontally continuous across the image.

In some examples, the method further includes imaging a selected portion of a subject's body with an ultrasound device having a movable transducer to provide the ultrasound scan image. In numerous cases of such examples, the determination of muscle tissue quality is performed essentially contemporaneously with the imaging of the subject with the ultrasound device for another purpose.

In some implementations, a non-invasive method of determining human muscle tissue quality or composition includes providing an ultrasound device having a movable transducer, the transducer operable in a high frequency range; selecting a target area of a subject; adjusting the ultrasound device for a depth of scan appropriate for the selected target area; disposing the transducer proximate to the subject and perpendicular to the selected target area; scanning the selected target area by processing ultrasound reflection received by the transducer to provide at least a partial scan image of the selected target area, the partial scan image provided by a plurality of pixels; blurring the pixels of the partial scan image; thresholding the pixels of the partial scan image to provide an image having black pixels which represent contractile muscle fibers, and white pixels which represent non-contractile tissue; distinguishing contractile tissue from remaining structural elements (e.g. fat, connective tissue, scars, and so on); and determining the muscle tissue quality based on the ratio of contractile tissue to non-contractile tissue. In some examples, one or more systems or apparatuses may perform this method.

In various examples, morphing the structural elements of the binary image to remove small structural elements and connect large structural elements is provided, The morphing is mathematical morphology. In some examples, the morphing includes applying a morphological function for opening.

In numerous examples, the method includes vertically cropping one or both sides of the partial scan image before blurring a remaining central portion of the partial scan image. In some cases of such examples, between $1/10$ and $1/5$ of the partial scan image is vertically cropped from one or both sides.

In some examples, the method is performed in about real time. In various examples, the method is about contemporaneously performed on different partial scan images from different locations about a subject's body.

In other implementations, a non-invasive method of determining human muscle intramuscular fat content includes receiving at least one ultrasound scan image of at least a portion of a skin layer as disposed above one or more additional tissue layers, the skin layer defining a horizontal axis and the ultrasound scan image provided by a plurality of pixels; blurring the pixels of the ultrasound scan image; thresholding the pixels of the ultrasound scan image to provide a trinary image having a plurality of structural elements of different sizes and gray scale; and determining the intramuscular fat content based on the plurality of structural elements of different sizes and gray scale. In some examples, one or more systems or apparatuses may perform this method.

In some examples, the method further includes reporting the intramuscular fat content. In numerous examples, the method further includes comparing the intramuscular fat content to a fat content goal. In various examples, the intramuscular fat content goal is based on a historic quality, qualities of other subjects, a performance objective, and so on. In some examples, the method includes reporting both the subject's muscle tissue quality and intramuscular fat content to the subject.

BRIEF DESCRIPTION OF THE DRAWINGS

The disclosure will be readily understood by the following detailed description in conjunction with the accompanying drawings, wherein like reference numerals designate like structural elements.

DETAILED DESCRIPTION

Figure 1:
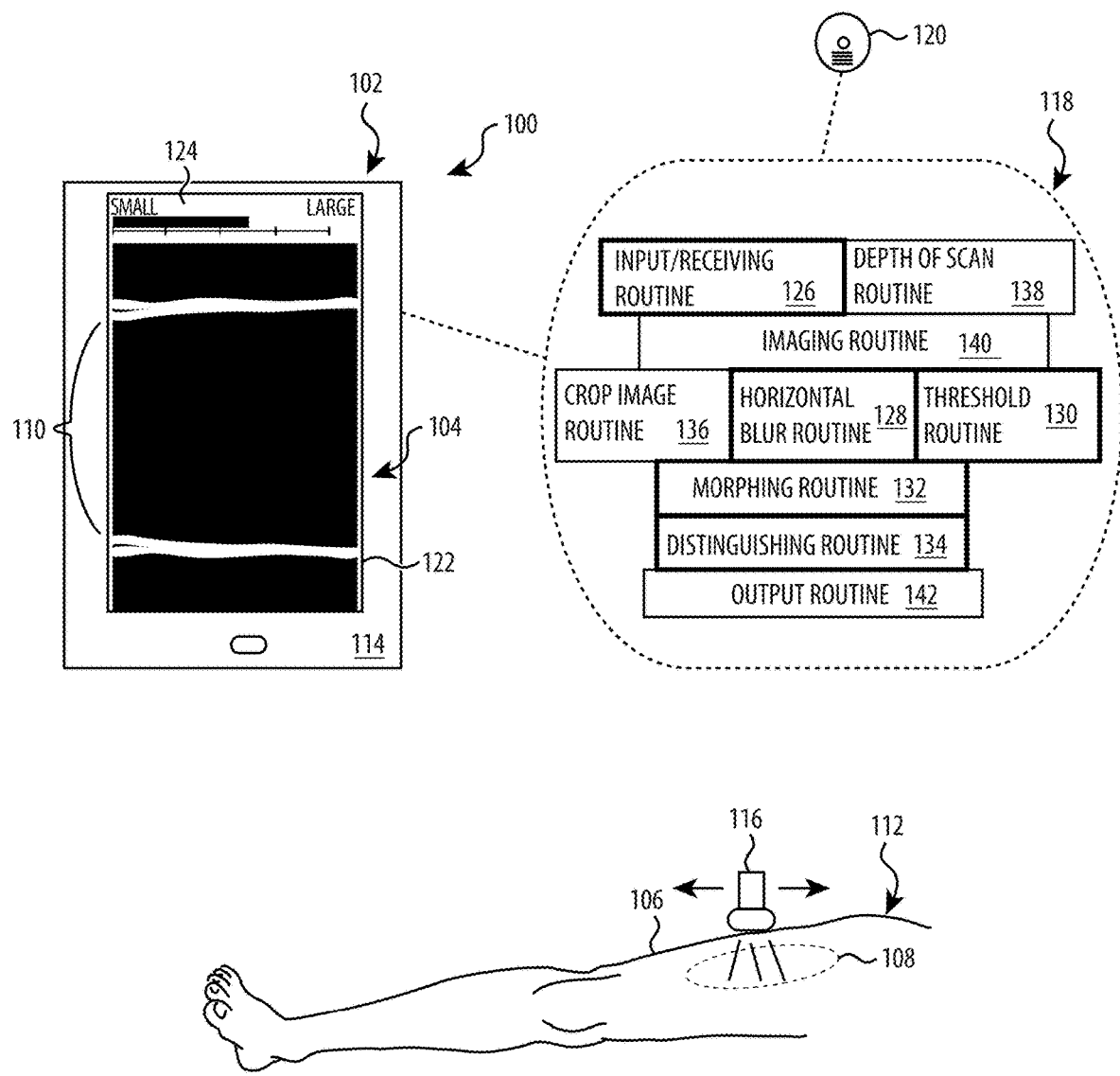
FIG. 1 depicts a high level block diagram of a system for non-invasive tissue evaluation that may be used to determine human muscle tissue quality or fat content in accordance with at least one embodiment.

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

The description that follows includes sample systems, methods, and computer program products that embody various elements of the present disclosure. However, it should be understood that the described disclosure may be practiced in a variety of forms in addition to those described herein.

Before proceeding with the detailed description, it is to be appreciated that the present teaching is by way of example only, not by limitation. The concepts herein are not limited to use or application with a specific system or method for non-invasive determination of muscle tissue quality or intramuscular fat. Thus although the instrumentalities described herein are for the convenience of explanation shown and described with respect to exemplary embodiments, it will be understood and appreciated that the principles herein may be applied equally in other types of systems and methods involving the determination of muscle tissue quality and specifically muscle tissue quality in humans.

The present disclosure relates to non-invasive determinations of a muscle tissue's overall quality. Muscle tissue quality herein refers to the composition of a muscle tissue, i.e., the constituents of the muscle tissue. In one embodiment, the muscle tissue quality is the ratio of contractile tissue to non-contractile tissue in the muscle tissue. Contractile tissue includes the contractile components of the muscle, i.e., muscle fibers, while non-contractile tissue includes components such as fat and connective tissue. Muscle tissue quality can also include a rating or grade, historic to the muscle tissue, as well as a simple absolute count. A high muscle tissue quality score indicates a fit muscle composed substantially of muscle fibers, whereas a low muscle tissue quality score indicates an amount of adipose (fat) tissue, scar tissue, connective tissue, and so on, in the muscle tissue, that could have a detrimental effect on the muscle tissue's strength, power, look and so on. The present disclosure also relates to non-invasive determination of a muscle tissue's fat content or intramuscular fat content. In these embodiments, the non-contractile components are further differentiated to identify fat tissue. The intramuscular fat content is the percent of total volume of a muscle that has been infiltrated by fat tissue, and is calculated by subtracting the content of fat in the muscle from the content of contractile components in the muscle and dividing by the total content of the muscle. Percent intramuscular fat can be used as a general health indicator for the subject, or as a prognosticator of possible health risks including obesity, dyslipidemia, glucose intolerance, cardiovascular disease, and general metabolic disorders associated with being overweight.

With regard to muscle tissue quality and intramuscular fat content, at least one ultrasound scan image of at least a portion of a skin layer as disposed above one or more additional tissue layers is received. The pixels of the ultrasound scan image are blurred, for example, horizontally blurred. The pixels of the ultrasound scan image are thresholded to provide an image having a plurality of structural elements of different sizes. The plurality of structural elements of different sizes are set to a gray scale based on the thresholded image. The structural elements of the image are optionally morphed to remove small structural elements and connect large structural elements, thereby forming an element composed of contiguous black pixels having a first range of values, and an element composed of contiguous white pixels having a second range of values. Muscle tissue is distinguished from remaining structural elements. The muscle tissue quality is determined as a ratio of the pixels that correspond to contractile tissue muscle fiber to pixels that correspond to all other non-contractile components and constituents. A high ratio of contractile fibers to non-contractile components indicates a fit, healthy or uninjured muscle, whereas a low ratio of contractile tissue to non-contractile components indicates an unfit, diseased or injured muscle. Muscle tissue quality can also be scaled or rated, for example, 1-100, to provide a relative indicator of the muscle's condition at the time of the image. The intramuscular fat content is determined by further differentiating the non-contractile components into fat tissue and non-fat tissue. The pixels that correspond to fat tissue in the muscle are subtracted from the pixels that correspond to contractile tissue, and a percent determined by dividing by the total number of pixels for the muscle. A relatively high percent of intramuscular fat indicates a muscle undergoing indicative changes associated with being overweight, the aging process, or various disease processes including dyslipidemia, glucose intolerance and/or cardiovascular disease.

In an embodiment, the black pixels correspond to contractile muscle tissue and the muscle tissue is identified as an element composed of contiguous black pixels. Likewise, the white pixels correspond to fat tissue and the fat tissue is identified as an element composed of contiguous white pixels. Furthermore, in an embodiment, determining the muscle tissue quality includes evaluating the ratio of black to white pixels.

Turning to FIG. 1, presented is a high level block diagram of a system for non-invasive tissue analysis (SNTA) 100. For at least one embodiment SNTA 100 is an evaluator 102 structured and arranged to evaluate at least one selected portion of an ultrasound scan image that has undergone image processing.

In the present example, the evaluator 102 evaluates an image 104 of at least a portion of a skin layer 106 disposed above one or more additional target tissues 108 to determine a quality of the muscle tissue 110. More specifically, the evaluator 102 evaluates the image 104 to determine a quality of muscle tissue 110 under the skin layer 106. The evaluator 102 may also evaluate the image 104 to determine an intramuscular fat content of the muscle tissue 110 under the skin layer 106.

As used herein, the term "skin" is understood and appreciated for its normal meaning as is expected in the medical profession—namely, an ever-changing organ that contains many specialized cells organized in three generalized layers—the epidermis, the dermis and subcutaneous tissue. Of course each of these layers may also be described as being comprised of multiple layers. With respect to the present disclosure and this description, the skin layer 106 is understood and appreciated to be one or more of the layers of epidermis, dermis and subcutaneous tissue. Precise identification and distinction of these layers may not be necessary for most embodiments. Indeed the identification of the skin layer 106 may serve generally as a point of reference in image 104. Moreover, in varying images, the skin layer 106 may be shown in an image as a portion of the subcutaneous tissue, a portion of the dermis and the subcutaneous tissue, and/or a portion of the epidermis and the dermis and the subcutaneous tissue.

As used herein the term "scan" is understood and appreciated for its normal meaning and as is expected in the medical profession—namely, "a. examination of the body or an organ or part, or a biologically active material, by means of a scanning technique such as ultrasonography—an ultrasound-based diagnostic imaging technique used for visualizing subcutaneous body structures; b. the image so obtained."

With respect to the present disclosure, and as is set forth in greater detail below and in the accompanying figures, the scan image is the element of importance. As such as used herein the terms "scan image," and or "image" are understood to be synonymous. Moreover, the ultrasound transducer provides a signal that for the present disclosure is rendered as an image comprised of a plurality of pixels. The present disclosure teaches the processing and evaluation of the resulting image, and not the processing, evaluation or transformation of the original ultrasound signal or waveform.

In at least one embodiment, SNTA 100 has a processor-enabled device such as computer 114. Computer 114 is adapted to receive the information from the ultrasound transducer 116 and provide a scan image of a portion of a skin layer 106 disposed above one or more additional target tissues 108, of the subject 112. For illustrative purposes the portion shown of the subject 112 is that of the right leg, but as will be further discussed below, SNTA 100 can be, and for at least one embodiment is, applied to multiple different locations of the subject's 112 body.

With respect to FIG. 1, SNTA 100 is at least in part conceptually illustrated in the context of an embodiment for a computer program 118. Such a computer program 118 can be provided upon a non-transitory computer readable media, such as an optical disc 120 or RAM drive that can be provided to a computer 114 to be adapted as SNTA 100. As is further shown and described in connection with FIGS. 10-16, in alternative embodiments the computer program 118 can be provided to a computer serving at least as part of an application providing platform, such as but not limited to the Apple App Store, that platform in turn operable to provide the computer program 118 to a computer 114 to be adapted as SNTA 100.

As will be discussed further below, SNTA 100 may be employed upon a computer 114 having typical components such as a processor, memory, storage devices and input and output devices. During operation, the SNTA 100 may be maintained in active memory for enhanced speed and efficiency. In addition, SNTA 100 may also be operated within a computer network and may utilize distributed resources.

In at least one embodiment, the SNTA 100 system is provided as a dedicated system to provide non-invasive tissue analysis. In at least one alternative embodiment, the SNTA 100 system is achieved by adapting an existing computer 114 which is portable, such as a smart phone (such as an iPhone® or Android®), tablet computer (such as an iPad®), an implant, a wearable device, and so on.

With respect to FIG. 1, SNTA 100 has been conceptually illustrated as a tablet computer 114, having a display 122 operable to display a visual representation of the scan image 104. The display 122 also is shown to provide an indicator 124 to inform an operator of the determined tissue analysis.

For at least one embodiment, the software may be described as including an input/receiving routine 126, a blurring routine, for example, a horizontal blurring routine 128, a threshold routine 130, an optional morphing routine 132, and a distinguishing routine 134. As is set forth and described below, the elements of SNTA 100 may be summarized for at least one embodiment as follows.

The input/receiving routine 126 is operatively associated with an input devices to receive the scan, such as a Digital Imaging and Communications in Medicine (DICOM) data file, and may also receive other information such as the subject's name, location, current state of exertion, etc. If not in image form, this received scan is provided to the operator as a scan image 104 comprised of a plurality of pixels. The blurring routine 128 is operable to horizontally or otherwise blur the pixels of the image. The thresholding routine 130 is operable to threshold each pixel to provide an image having a plurality of structural elements of different sizes and of different gray scale. The thresholding routine is adapted to recognize and grade the impedance of contractile and non-contractile tissue. The optional morphing routine 132 is operable to morph elements of the processed image to remove small structural elements and connect large structural elements. The distinguishing routine 134 is operable to distinguish contractile tissue from remaining structural elements, and determine the muscle tissue quality by taking the distinguished contractile tissue and evaluating a ratio of contractile to non-contractile tissue. Where intramuscular fat is concerned, the thresholding routine is adapted to recognize and grade the impedance of contractile and fat tissue, such that the distinguishing routine 134 is operable to provide a percent intramuscular fat.

For at least one embodiment, SNTA 100 may also include an optional cropping or crop image routine 136. As has been noted above and will be further understood and appreciated with respect to the following description, the present disclosure advantageously is distinguishing a subject's muscle tissue quality and intramuscular fat percent through image processing. More specifically image processing techniques including blurring, thresholding, and morphing are advantageously combined so as to process a scan image and provide processed image 104 in such a way as to quickly and very accurately distinguish contractile muscle fiber from non-contractile components, and further distinguish non-contractile components into fat and non-fat tissue. The result is a muscle's muscle tissue quality, and where evaluated, intramuscular fat. In other embodiments, image processing techniques of blurring and thresholding are combined so as to process a scan image and provide a process image that can be quickly and accurately distinguished to the quality of a muscle tissue or the content of fat in a muscle tissue.

In this respect, for at least one embodiment, between 1/10th and 1/5th of the image is vertically cropped from one or both sides so as to leave a more central portion of the original scan image for subsequent image processing. For at least one alternative embodiment, no cropping is performed.

In addition to the core routines, an input/receiving routine 126, a blurring routine 128, a threshold routine 130, an optional morphing routine 132, and a distinguishing routine 134, in at least one alternative embodiment, SNTA 100 further includes an ultrasound device having a movable transducer 116 operable in a high frequency range and has an adjustable depth of scan. More specifically, the high frequency range may be between about 5 to 20 megahertz. In addition the depth of scan may be between about 1 centimeter and about 7 centimeters. For at least one embodiment, the ultrasound transducer 116 may be an existing commercially available and FDA approved ultrasound transducer 116 incorporated as part of SNTA 100 without departing from the scope of FDA approval for the operation of the ultrasound transducer device. In some embodiments, the ultrasound device may be operated at a frequency that optimizes the acoustic impedance of tissue density between contractile and non-contractile tissue, and within non-contractile tissue, fat and non-fat tissue.

For at least one embodiment of SNTA 100, the computer program 118 may additionally include a depth of scan routine 138, an imaging routine 140, and optionally an output routine 142. Moreover, the depth of scan routine 138 is operable to adjust the ultrasound device, e.g., ultrasound transducer 116, for a depth of scan appropriate for the target tissues 108. In at least one embodiment, the proper depth of scan is set based on the selection of target tissues 108 as indicated by an operator of SNTA 100.

The imaging routine 140 is operable to direct the movable transducer 116 to scan the selected target tissues 108 by processing ultrasound reflection received by the transducer 116 to provide at least a partial ultrasound scan of the selected target muscle. In at least one embodiment, the imaging routine 140 is structured and arranged to operate with a third party ultrasound imaging software provided to the computer 114.

For at least one embodiment, the optional output routine 142 is operable to output the scan of the target tissues 108 to a storage device, or database. This output routine may also be configured to provide an audible, visual or tactile output to inform the operator of SNTA 100 of the determined muscle tissue quality and/or percent intramuscular body fat.

With respect to FIG. 1, it is understood and appreciated that the elements, e.g., input/receiving routine 126, blurring routine 128, threshold routine 130, morphing routine 132, distinguishing routine 134, crop image routine 136, depth of scan routine 138, imaging routine 140, output routine 142, ultrasound transducer 116 and computer 114 are in at least one embodiment located within a single device. In at least one alternative embodiment, these elements may be distributed over a plurality of interconnected devices. Further, although each of these elements has been shown conceptually as an element, it is understood and appreciated that in varying embodiments, each element may be further subdivided and/or integrated with one or more other elements.

Figure 2:
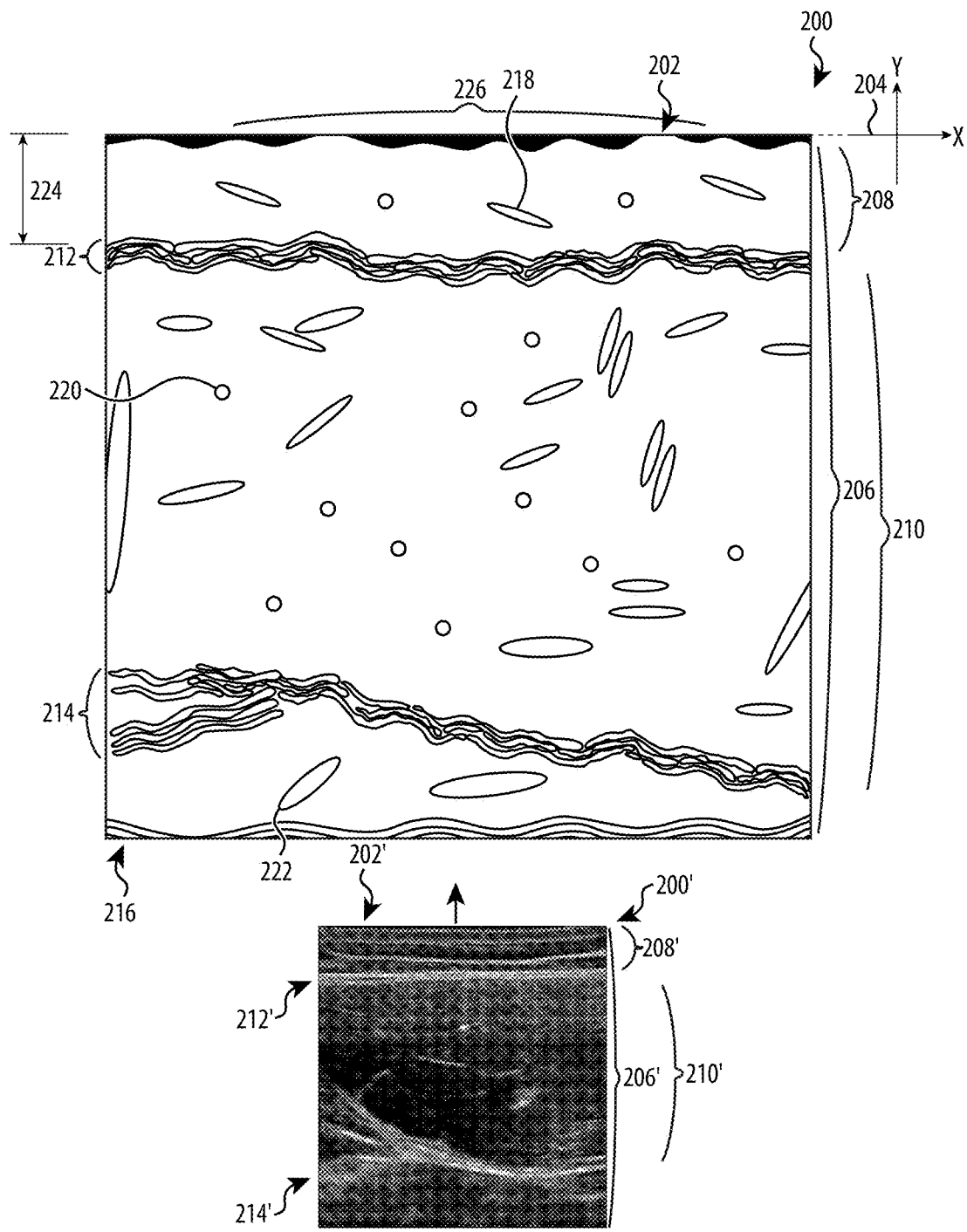
FIG. 2 depicts a conceptual illustration of an ultrasound scan of target tissues in accordance with at least one embodiment.
Figure 3:
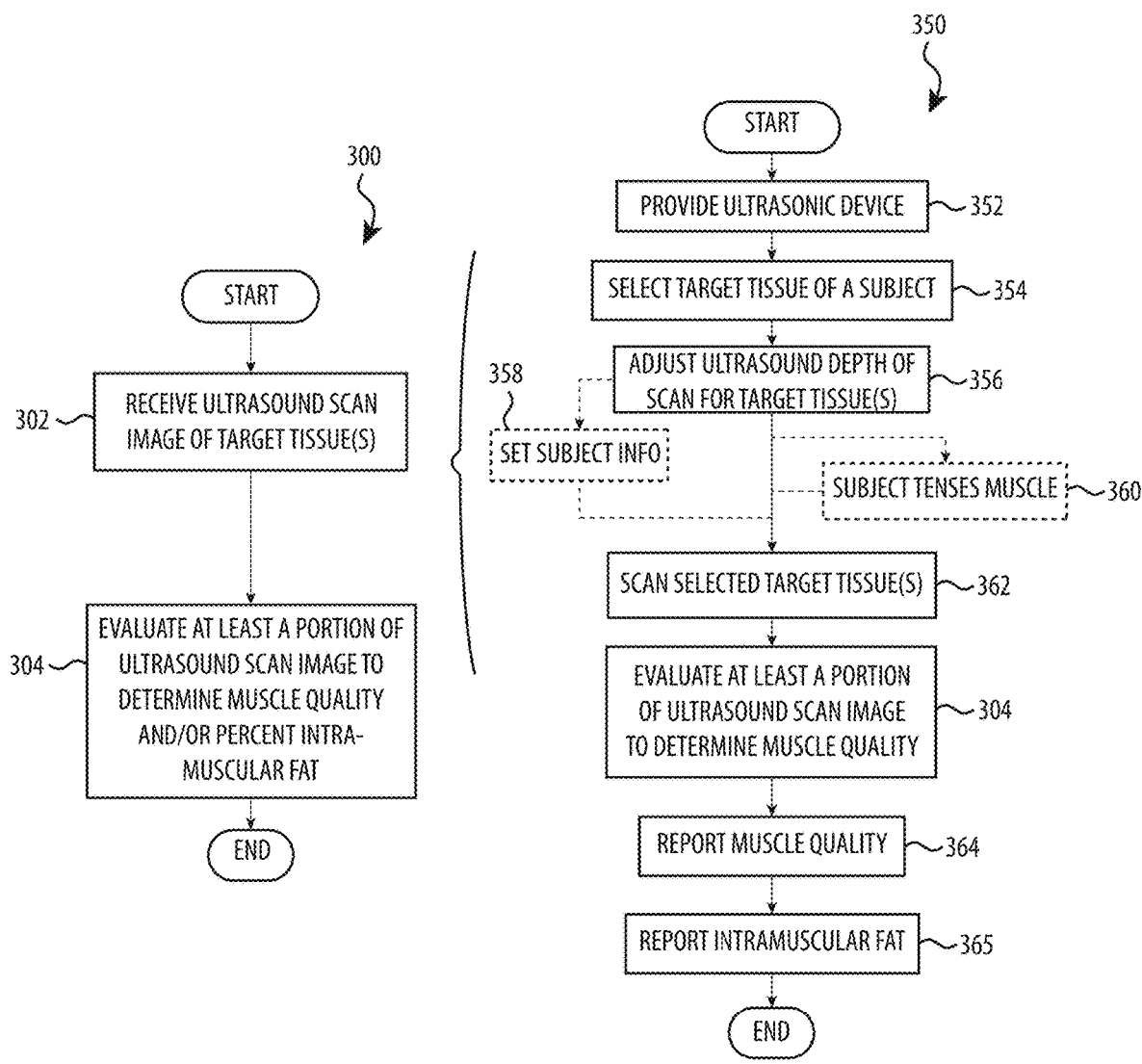
FIG. 3 depicts a high level flow diagram for a method of non-invasive determination of human muscle tissue quality and/or fat content in accordance with at least one embodiment.
Figure 4:
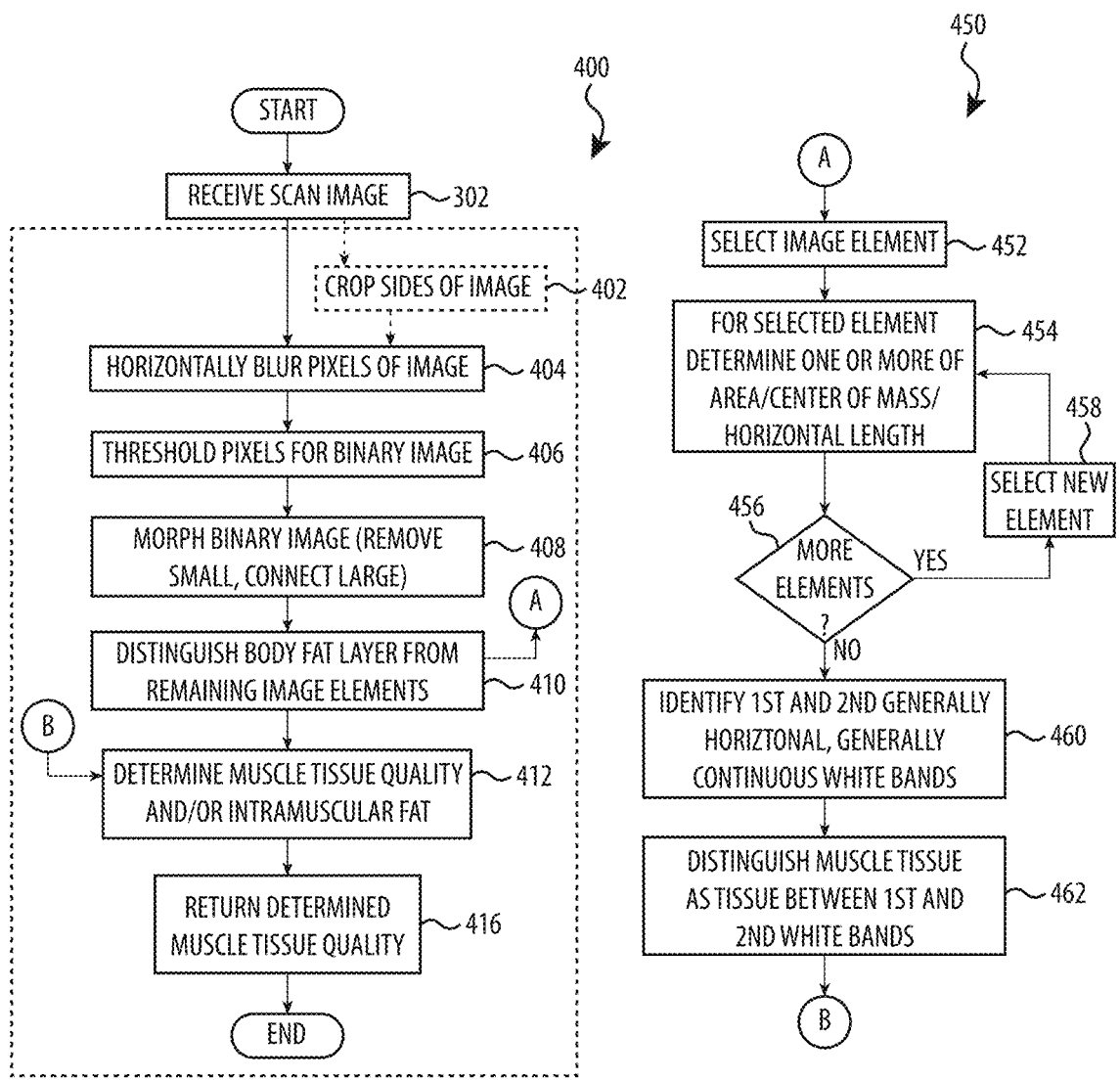
FIG. 4 depicts a refined flow diagram for the evaluating operation for non-invasive determination of human muscle tissue quality and/or fat content in accordance with at least one embodiment.

FIGS. 3 and 4 in connection with FIGS. 1, 2 and 5-9 provide a high level flow diagram with conceptual illustrations depicting methods 300, 350, 400, 450 for non-invasive determination of human muscle tissue quality and/or intramuscular fat content in accordance with at least one embodiment. It will be appreciated that the described method(s) need not be performed in the order in which it is herein described, but that this description is merely exemplary of one method of non-invasive determination of human muscle tissue quality. It will also be appreciated that the described method(s) may also relate to the non-invasive determination of intramuscular fat in accordance with at least one embodiment.

As is shown in FIG. 2, an enlarged conceptual ultrasound scan image 200 is shown corresponding to a real ultrasound scan image 200'. Typically ultrasound scan images such as scan image 200' are rendered in black and white in accordance with a grey scale, though color is certainly an option and within the scope of the present disclosure. Various structures with a subject's body reflect the ultrasound signal with varying intensity. In general there are two distinct patterns of reflection that give rise to the echoes that make up the ultrasound image—specular reflections and scattering reflections.

Specular reflections are responsible for the bright appearances of fibrous structures such as tendons, ligaments and the boundaries between different types of tissues. Scattering reflections gives rise to the characteristic texture of an image seen within soft tissues. The scan image 200' is composed of a plurality of pixels. Scan pixels may correlate directly with image pixels as used to render scan image 200. Of course, in some embodiments the resolution of the scan pixels may be greater than the resolution applied in the scan image, such that each pixel of the scan image may correlate to two or more pixels of the scan.

Those skilled in the art of ultrasound imaging can and often do perceive a great deal of information from images that are otherwise perhaps visually interesting but also perhaps largely unintelligible to the untrained eye.

Through image processing as performed by SNTA 100 and method 300, this training to perceive and differentiate structures within a typical ultrasound image is for all intents and purposes eliminated. For ease of discussion, conceptual rendering of ultrasound images has been provided to ease and facilitate this discussion.

Moreover, as shown in FIG. 2, the scan image 200 may capture a portion of the surface tissue 202, such as the skin at the top of the images, which defines a horizontal axis 204 for the scan image 200. The scan image 200 also shows at least a portion of subcutaneous tissues 206, which likely includes a body fat tissue 208 having a thickness 224, an as yet not clearly delineated area of muscle tissue 210, and other tissues such as fibrous tissues 212 and 214, bone tissue 216 and so on, of which 218, 220 and 222 are exemplary. This same variety of tissues is of course evident in real ultrasound scan image 200', a subset of which have been suggestively identified with like numbers 202', 206'-214'.

Moreover, scan image 200 provides enough information to discern the presence of non-contractile components within the muscle tissue (see below). Indeed, embodiments of the present disclosure may apply image processing techniques so as to clearly distinguish at least the muscle tissue 210 and the fat layer 208. Scan image 200 also provides enough information to discern the presence of infiltrated fat, fibrosis (scar tissue), and connective tissue into the muscle tissue 210. Scar and connective tissue, having a greater density, show as items 208. Infiltrated fat tissue is closer in impedance to muscle tissue, and is therefore more difficult to distinguish overtly. Distinguishing the infiltrated or present fat, scar, connective, and other like tissue from the contractile muscle fiber or tissue provides an indicator of the quality of the muscle tissue 210. A high percentage of fat or other non-contractile components in the contractile muscle tissue indicates a lower quality muscle tissue, than a low percentage of fat and other non-contractile components in the muscle tissue 210. Embodiments herein distinguish contractile from non-contractile tissue to grade a muscle tissue's quality. Further, distinguishing fat from non-fat in the non-contractile components, is an indicator in the contractile muscle tissue of a percent intramuscular fat. A high percent of intramuscular fat may be an indicator of being overweight, of age related decline in the muscle, or as an indicator of a disease state, for example, dyslipidemia, glucose intolerance or cardiovascular disease.

As noted above and further described below, for at least one embodiment, between $\frac{1}{10}$th and $\frac{1}{5}$th of the image is vertically cropped from one or both sides so as to leave a more central portion 226 of the scan image 200 for subsequent image processing. This cropping is more fully illustrated with respect to FIG. 5.

Further, although the illustrations and discussion provided herein for exemplary purposes generally appear to be 2D (two dimensional) images, the system and methods are equally applicable multi-axis ultrasound imaging techniques, such as for example 3D ultrasound.

FIG. 3 provides a high level flow diagram depicting a method 300 for non-invasive determination of muscle tissue quality, which is more fully appreciated with respect to FIGS. 2 and 5-9 providing both real and conceptual illustrations of ultrasound scan images as processed in accordance with at least one embodiment. It will be appreciated that the described method, as well as all other subsequent methods and refinements to the disclosed methods need not be performed in the order in which they are herein described, but that the descriptions are merely exemplary of a method or methods that could be performed for non-invasive muscle tissue quality determination. It is also appreciated, that the described method may be further modified for non-invasive determination of percent intramuscular fat, where requested or needed.

As shown in FIG. 3, method 300 commences with receiving an ultrasound scan image of target tissue(s), block 302. An exemplary scan image such as scan image 200 is shown in FIG. 2. Moreover, even though contractile muscle tissue and non-contractile tissue therein may be the primary tissues of interest in one setting, for the intramuscular fat content to be accurately determined under the present disclosure, it may be desirable to distinguish the contractile muscle tissue from fat tissue and other more fibrous tissues, like connective tissue and scar tissue. In addition, as the contractile muscle tissue is captured in ultrasound scans often performed with an intent to image other tissues, such scan images may also be processed under the present disclosure for about real time or later analysis of muscle tissue quality and/or percent intramuscular fat. Indeed, substantially real time analysis to determine a subject's muscle tissue quality or percent intramuscular fat may be performed as a specific procedure, or as a beneficial ancillary procedure when a subject is undergoing an ultrasound imaging process for another purpose (such as determination of glycogen stores, determination of overall body fat, and so on).

Moreover, scan image 200 may be provided as described above through the use of SNTA 100 in an embodiment providing an ultrasound transducer 116, or through another ultrasound imaging system and/or process. For at least one embodiment the ultrasound scan image is provided by the system(s) and methods as set forth in U.S. Pat. No. 8,562,529 entitled Method and System for Non-Invasive Determination of Glycogen Stores, U.S. Pat. No. 8,517,942 entitled Method for Non-Invasive Determination of Glycogen Stores, U.S. Pat. No. 8,512,247 entitled System for Non-Invasive Determination of Glycogen Stores, U.S. patent application Ser. No. 14/012,538 entitled System and Method for Target Muscle Glycogen Score Determination and Evaluation, and U.S. patent application Ser. No. 14/491,553 entitled System and Method for Non-Invasive Determination of Human Body Fat—each of which is incorporated herein by reference.

With the scan image 200 now received, method 300 continues with the evaluation of at least a portion of the scan image 200 to determine muscle tissue quality and/or intramuscular fat, block 304. For application of method 300, an embodiment of SNTA 100 need not have, or otherwise be coupled to, an ultrasound transducer 116. Method 300 may also be performed by SNTA 100 when a user desires to review historical data of tissue scans, such as for example to revisit past histories of evaluation to perceive changes in development and potential adjustments to a subject's training methods, general activities, age, diet, health or other form of activity and/or medication.

Of course, for real time non-invasive determination of muscle tissue quality and/or percent intramuscular fat, in varying embodiments SNTA 100 may indeed include an ultrasound transducer 116 as described above. As such, method 300 may be augmented as method 350, the augmentation as illustrated pertaining to at least one method of providing the received ultrasound scan image 200.

More specifically, for augmented method 350, an ultrasound transducer 116 is provided as part of SNTA 100, block 352. A target tissue, such as a muscle, e.g. target tissue(s) 108, is selected, block 354. As noted, the ultrasound transducer has an adjustable depth for scanning, such as a selection between about 0.5 and 10 centimeters. The ultrasound transducer 116 is adjusted to provide a depth of scan appropriate for the selected target tissue, block 356.

In at least one embodiment, the depth of scan is adjusted manually, such as to about 3.5 centimeters for the skin, body fat, and rectus femoris muscle. In an alternative embodiment, the depth of scan is automatically selected by an operator selecting a desired tissue, such as a muscle tissue, e.g., rectus femoris, vastus lateralis, or biceps. In addition, in varying embodiments, the auto-determined and set depth may also be adjustable by the operator so as to permit adjustment for various body types.

In at least one embodiment, additional and optional information about the subject is recorded, as indicated by dotted block 358. This optional information may include, but is not limited to, details such as the subject's name, age, gender, time of day, status of subject—at rest/at VOT Max, after eating, or other such information desired to be recorded and displayed in connection with the scanned image of the target muscle.

Moreover, to summarize for at least one embodiment, the augmented method 350 includes providing an ultrasound device having a movable transducer, the transducer operable in a high frequency range, selecting a target tissue 108 of a subject 112 and adjusting the ultrasound device for a depth of scan appropriate for the selected target tissue 108.

As the ultrasound transducer 116 operates by providing a high frequency signal that is directed into tissue and detecting reflections returned by encountered elements, it is understood and appreciated that the transducer should be aligned generally perpendicular to the selected target muscle. Of course, if a transducer having an alignment configuration that is other than perpendicular is employed, the specific alignment as intended for the transducer should be used.

It is understood and appreciated that an ultrasound transducer 116 may be positioned along the longitudinal or latitudinal axis of the tissue or somewhere in between. For general alignment purposes and ease of operation, in general the operator of the system will select ultrasound transducer 116 alignment matching to either the longitudinal or latitudinal axis of the target tissue 108.

Testing has determined that a key factor for deciding which alignment to use is perhaps the initial quality of the scan image. In other words, for at least one embodiment, at least a longitudinal and a latitudinal image of the target tissues is obtained so that the images can be compared by the operator and/or SNTA 100 to determine which image is best for analysis.

Application of the ultrasound transducer 116 against the subject's skin can be a practiced skill, for if too much pressure is applied the transducer may inadvertently compress the tissue and thereby hamper the quality of the scan and the resulting evaluation of muscle tissue quality. However, an easy solution presents itself that substantially minimizes the risk of transducer related compression of the tissue.

As shown by optional dotted block 360, the subject can simply tense his or her muscle if it is the target tissue 108 or directly below the target tissue. More specifically, if the subject acts to tense his or her muscles adjacent to the desired target tissue, the natural action of the muscle contraction causes the muscle to swell and thereby resist compression. The contracted and thereby enlarged muscle may also be advantageous in providing an even clearer cross sectional scan than may be obtained with a relaxed muscle.

In short, while the quality of the scan for the tensed or un-tensed muscle adjacent to the target tissue 108 may be the same for an operator skilled in how much pressure to apply, for the novice, as well as the skilled operator, tensing an adjacent muscle does not appear to significantly hamper the determination of muscle tissue quality or intramuscular fat and may help insure greater consistency of scans in a wide variety of locations and settings. Indeed, for at least one embodiment, when the method of scanning a target tissue(s) 108 is performed, the subject will tense his or her adjacent muscle as a normal and expected part of the scanning process.

Moreover, to achieve the scan of the target tissue 108, the ultrasound transducer 116 is disposed proximate to the target tissue 108 and as the ultrasound transducer 116 is activated the target tissue(s) 108 is scanned, block 362. In at least one embodiment the ultrasound transducer 116 is placed in direct contact with the subject's skin. In at least one alternative embodiment, a protective cover, shield or even the subject's clothing is disposed between the ultrasound transducer 116 and the subject's skin.

A scan image is then provided from the resulting scan, and evaluated as noted above, block 304. A report of the determined muscle tissue quality may also be reported, block 364. In some instances a report of the determined intramuscular fat may also be reported 365.

In other words, to summarize for at least one embodiment, the augmented method 350 continues with disposing the transducer proximate to the subject 112 and perpendicular to the selected target tissue 108, and then imaging the selected target tissue 108 by processing ultrasound reflection received by the transducer to provide at least a partial scan of the selected target tissue 108. Many ultrasound transducers provide images as cross sections of the tissues and structures whereas others may provide 3-D views. For consistency in analysis, in at least one embodiment the operator of SNTA 100 adopts a convention to scan a target tissue along its long axis or short axis.

For the majority of leg and arm tissues the long axis is generally parallel to bone structure and the short axis is generally perpendicular to bone structure. Indeed in some embodiments, scans with SNTA 100 may be performed substantially contemporaneously along both the long and short axes of a target tissue 108 for enhanced comparison and analysis.

Method 350 then continues with the evaluation of the scan as discussed above with respect to block 304. For at least one embodiment, it is understood and appreciated that the evaluation of the image 104 is performed about contemporaneously with the scanning of the target tissue 108.

The determined muscle tissue quality is then reported to the operator, block 364. The determined muscle tissue quality may also be recorded for use in plotting the changes in a subject's muscle tissue quality over time, and/or in response to various different points of exercise, conditioning, diet, medication, age, disease state, and other factors. The muscle tissue quality can be reported as a ratio of contractile muscle fiber to non-contractile components, as a rating or grade or as a simple absolute count. Each report provides information useful for the subject to tract and improve muscle quality. Optionally, the determined intramuscular fat content may also be reported to the operator 365. The determined intramuscular fat may be reported alone or in conjunction with the determined muscle tissue quality. As for muscle tissue quality, the intramuscular fat content can be plotted for a subject as related to time, exercise, conditioning, diet, medication, age, disease state and the like. Intramuscular fat can be reported as a percent, i.e., percent of the muscle that is fat tissue, as a grade, or as an absolute number.

FIG. 4 in connection with FIGS. 5-9 provides a high level flow diagram with conceptual illustrations to further refine at least one embodiment of method 300 for evaluating at least a portion of the ultrasound scan image to determine muscle tissue quality and/or intramuscular fat content. Moreover in FIG. 4, method 400 corresponds in greater detail to block 304 of FIG. 3. Again, it is appreciated that the described method need not be performed in the order in which it is herein described, but that this description is merely exemplary of one method for non-invasive determination of human muscle tissue quality and/or non-invasive determination of human intramuscular fat content.

More specifically, as FIG. 4 expands on FIG. 3, initially a scan image of the target tissues 108 is received, block 302. An exemplary image scan is conveniently provided as scan image 200 as shown and described above with respect to FIG. 2.

Figure 5:
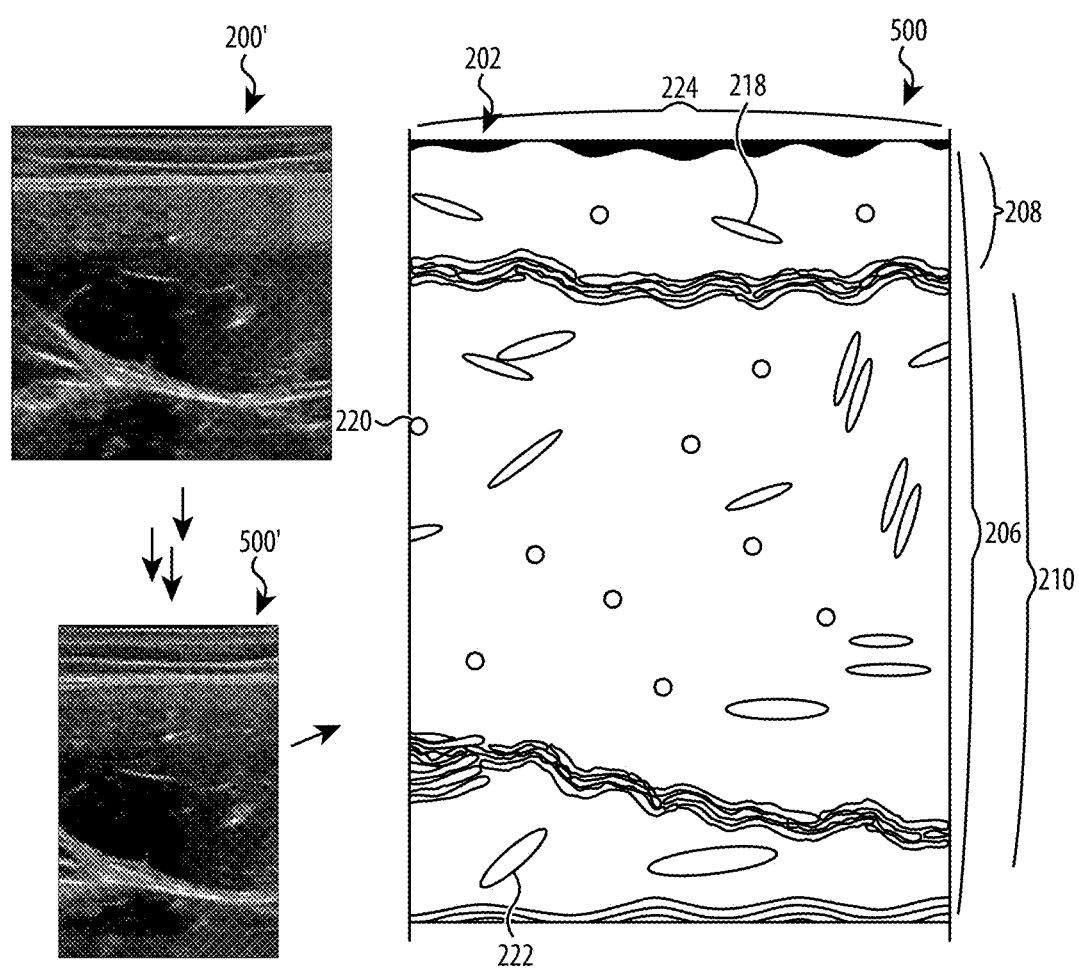
FIG. 5 depicts a conceptual illustration of a cropped ultrasound scan image in accordance with at least one embodiment.

Ultrasound scan images tend to image tissues directly below the transducer most clearly, with the side areas of the scan tending to be less clear. For purposes of subsequent image enhancement, for at least one embodiment one or both sides of the scan image 200 are cropped as is shown in FIG. 5 as cropped scan image 500. Moreover, cropped scan image 500 is the more central portion 226 of scan image 200 shown in FIG. 2. Although embodiments of method 300 may be performed without side cropping, in general between ⅒ and ⅕ of the image is vertically cropped from each side as suggested by dotted lines and optional block 402.

With respect to FIG. 5, as with FIG. 2 above the conceptual cropped scan image 500 is shown to generally corresponding to real cropped ultrasound scan image 500'.

Figure 6:
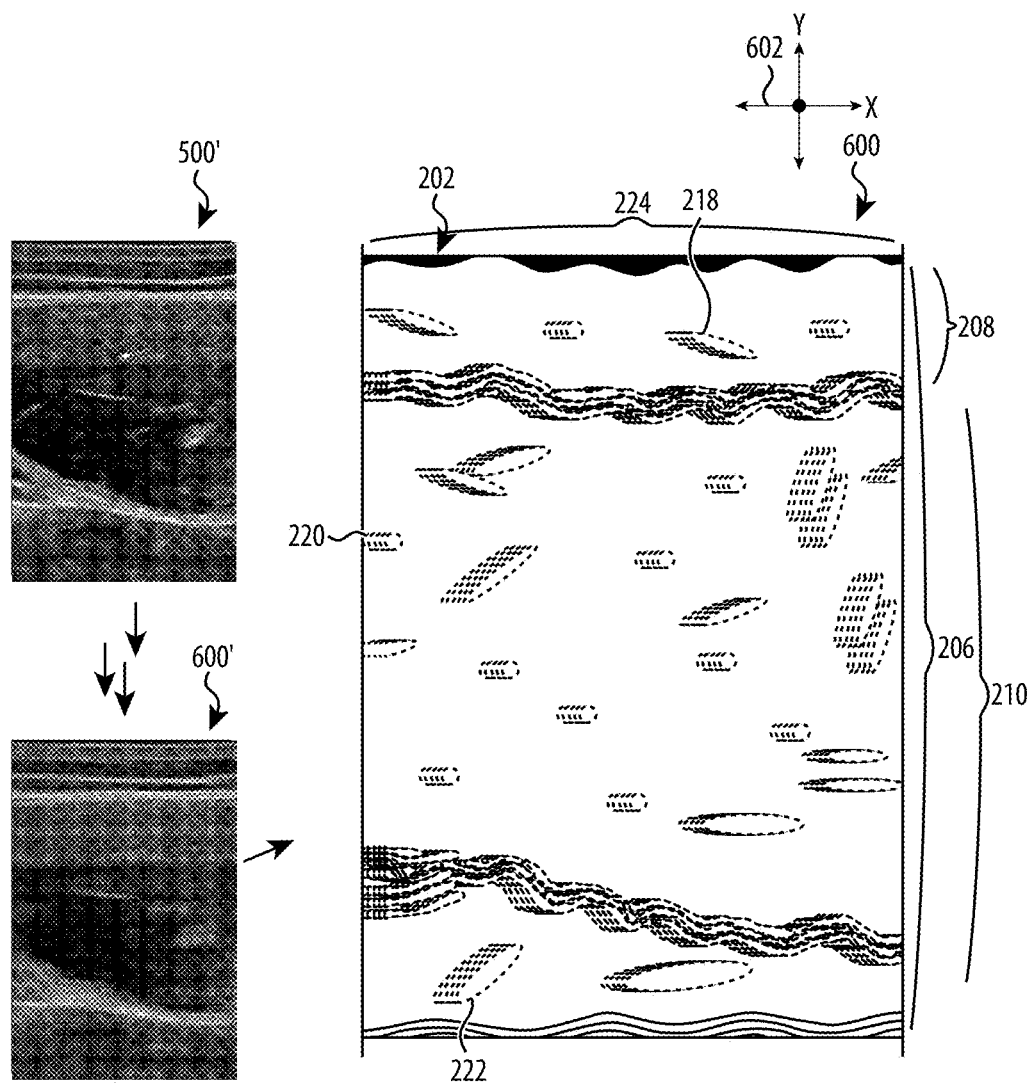
FIG. 6 depicts a conceptual illustration of a horizontally blurred ultrasound scan image in accordance with at least one embodiment.

Next, method 400 proceeds to blur the pixels as shown in, for example, the horizontally blurred scan image 600 in FIG. 6, block 404 (see FIG. 4). Again blurred scan image 600 conceptualizes blurred real ultrasound scan image 600'.

Traditionally the clarity of an ultrasound image and indeed the sharpness of the elements within the ultrasound image are very important. This is quite understandable as often times an ultrasound image is used to guide a doctor in surgery, so clear imaging is important for both the doctor and the patient.

For the present disclosure, sharpness of detail within the image may not be important. In fact, the present disclosure teaches how image processing techniques may be applied so as to remove elements of small detail and enhance the ultimate distinguishing of more dense contractile muscle fiber from non-contractile components (fat, connective tissue, scar tissue, etc). In image processing, a kernel such as a convolution matrix, mask or filter is a small matrix that can be applied to propagate a change in a source image for a desired effect. Moreover the change imparted is a result of convolution between an applied kernel and an image.

Blurring is an image processing technique commonly applied so as to reduce noise and reduce detail. Blurring functions are well understood and known to those skilled in the art and need not be discussed in detail here.

A high level discussion of blurring is provided so as to facilitate general understanding of the process so as to further appreciate the advantageous achievement of SNTA 100 and method 300. In simple terms, blurring an object means that each of the pixels in the source image gets spread over and mixed with surrounding pixels. With respect to the present disclosure, blurring may be achieved by application of a Mean Filter, Weighted Average Filter, Gaussian Filter or other appropriate filter. A Mean Filter is also known as a Box Filter or Average Filter, and is understood to have the following properties—it is odd ordered, the sum of all elements should be 1 and the elements of the filter are the same. A Weighted Average Filter acts as the name implies—giving more weight to the center value. Here again it is odd ordered, the sum of all elements should be 1, but the weight of the center element should be more than all of the other elements. A Gaussian Filter is one that uses a Gaussian function, which also expresses the normal distribution in statistics, for calculating the transformation to apply to each pixel in the image.

In one embodiment, blurring is only applied along the horizontal axis. As such a 1×3 Mean Filter or a one dimension Gaussian Function is typically appropriate. For at least one embodiment, the blurring filter is a 1 dimensional Gaussian function:

$$G(x) = \frac{1}{\sqrt{2\pi\sigma^2}} e^{-\frac{x^2}{2\sigma^2}}$$

For at least one alternative embodiment, a 1×3 Mean Filter such as [⅓, ⅓, ⅓] is applied.

As is shown in FIG. 6, in conceptually blurred image 600, the tissue elements such as 222 and 224 have been blurred along the horizontal X axis as indicated by coordinate axis 602. No blurring has occurred along the vertical Y axis. As such the edge distinctions along the horizontal axis are less sharp as blurring makes the collections of similar pixels either bigger or smaller. And again, conceptual blurred image 600 corresponds generally to real blurred image 600'.

Figure 7:
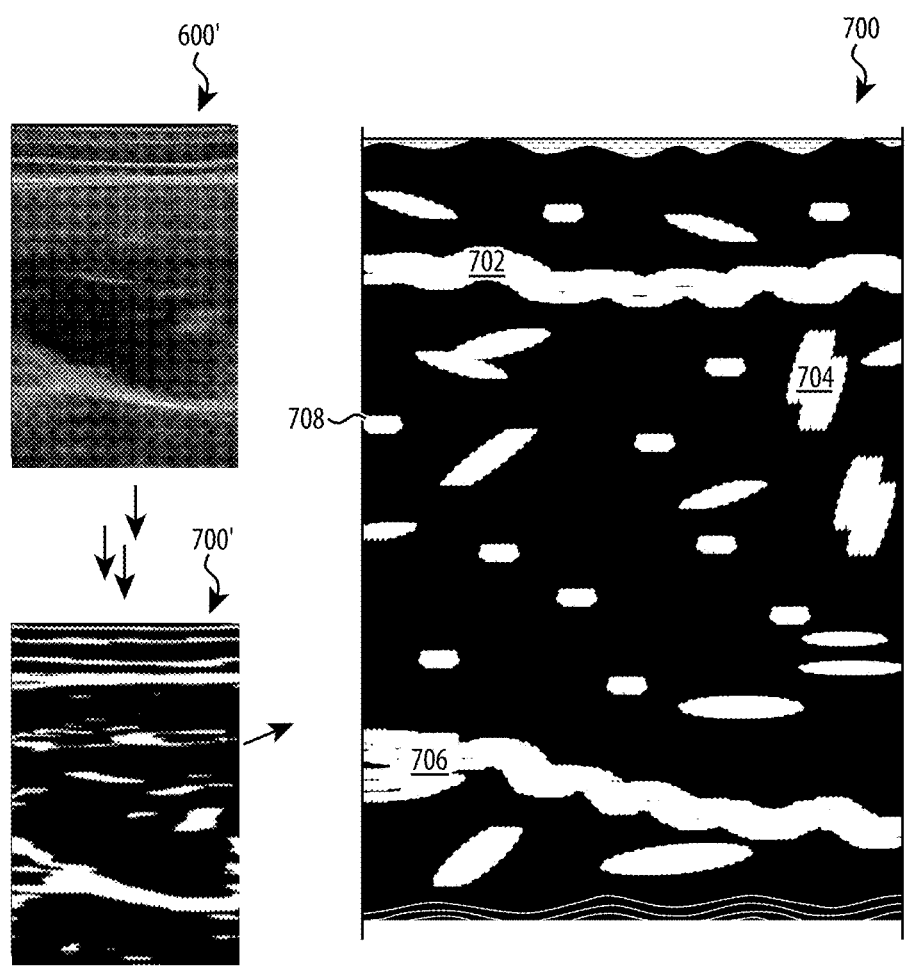
FIG. 7 depicts a conceptual illustration of a thresholded horizontally blurred image to provide an image in accordance with at least one embodiment.

Next, method 400 proceeds to threshold the pixels of the blurred image 600 to either black or white to provide an image 700, block 406, as shown in FIG. 7. Conceptual binary image 700 corresponds generally to actual image 700'. At this stage, black images correspond to contractile muscle fiber, while white images correspond to non-contractile components having a higher echo intensity (and therefor a brighter image).

Thresholding is a method of image segmentation and is well known to those skilled in the art and need not be discussed in detail herein. A high level discussion of thresholding is provided so as to facilitate general understanding of the process so as to further appreciate the advantageous achievement of SNTA 100 and method 300. From a gray scale image, thresholding may be used to create a binary image, such as binary image 700 from blurred scan image 600.

In one embodiment, each pixel of the blurred scan image 600 has a value equal to or ranging from black (i.e., 0-125) to white (i.e., 126-250). To threshold the pixels, those between 0 and 125 are reset at black, those between 125 and 250 are reset at white. Of course this scale is merely exemplary and an alternative scale may be used. For example, thresholding an image to separate foreground (white) elements, from the background (non-white) elements. Logic is used to determine which background elements to do the analysis on. The analysis consists of calculating the amount of foreground elements within the larger background of non-white elements.

In addition, although color is the attribute for thresholding as described herein, in alternative embodiments thresholding may be applied to another color, luminance, darkness, contrast or other identifiable attribute of each pixel. Further, although thresholding is discussed using the two values, use of other threshold values is possible and contemplated. In various implementations, the threshold value may be set according to the particular apparatus used to obtain the image. In one embodiment, where intramuscular fat is analyzed, the reset black pixels corresponds to the impedance of contractile muscle fiber, gray to the impedance of fat, and white pixels correlate to the impedance of connective and scar tissue. Using this thresholding, the intramuscular fat content may be determined by distinguishing between gray and white pixels. Alternative values can be used to correlate and provide additional information related to black and white, or black, white and gray, dependent on the quality of the scan, the frequency of the device, and the size and depth of the muscle tissue being tested.

An noted above, the present disclosure in further processing the scan image, can provide a trinary image that has three possible values for each pixel (black, gray or white). Other threshold valuations can be used to distinguish muscle tissue quality or intramuscular fat, for example, using additional values to distinguish scar tissue from other connective tissue, or tissue having a distinct impedance by ultrasound from muscle tissue, for example, tissue necrosis from other areas of the muscle.

In one method, a ratio of black image to white image between the distinguished tissue boundaries provides muscle tissue quality. The black and white areas can be calculated as is well known in the art, including the use of scanning programs that total the number of black pixels to white pixels, use of image analysis, use of scanning calculators, and the like. As discussed further below, a determination of higher black area indicates a higher quality muscle than does a lower ratio of black to white area. With regard to percent intramuscular fat, the black, gray and white areas can be calculated to identify the total number of black pixels (contractile tissue), gray pixels (fat tissue) and white pixels (non-fat tissue). The gray pixels provide an area of fat tissue within the total muscle (black, white and gray pixels). The adjusted gray pixels (only fat tissue) is subtracted from the black pixels and divided by the total (black, white and gray) to provide the percent intramuscular fat. Muscle quality may also be calculated and characterized as a percentage, rating, grade, or absolute count as is beneficial to the subject and operator.

In another method, a ratio of area of white image to area of gray image between the distinguished tissue boundaries provides muscle tissue quality with respect to percent scar tissue. The area can be calculated as is well known in the art to provide a ratio of scar tissue to muscle fiber in the delineated area. Here white pixels provide connective or scar tissue within the total muscle (black, white and gray). The adjusted white is subtracted from the black pixels and divided by the total to provide a percent connective tissue for the muscle.

In one embodiment, particularly where contractile to non-contractile tissue is of primary concern, method 400 optionally proceeds to morph the remaining elements of the binary image 700 to remove small elements and connect large elements. To "morph" or "morphing" refers to mathematical morphology—a technique for the analysis and processing of geometric structures based on set theory, lattice theory, topology and or random functions and is a known technique applied to digital images. The basic morphological operators or morphological functions as they are also known are erosion, dilation, opening and closing. These morphological functions are well known to those skilled in the art and need not be discussed in detail herein.

A high level discussion of morphing, a.k.a. mathematical morphology, is provided so as to facilitate general understanding of the process so as to further appreciate the advantageous achievement of SNTA 100 and method 300.

The basic idea in morphology of a binary image is to probe an image with a simple, predefined shape such as a disc, square, cross or other simple geometric shape which is referred to as a structuring element and is itself a binary image. Opening removes white "holes" while closing removes black "holes." In accordance with at least one embodiment, the morphological function applied to further process the scan image so as to distinguish the muscle tissue quality is the morphological function of opening.

Opening is obtained by eroding an image following by then dilating the image. The erosion of a binary image A by the structuring element B (a disc of radius r) in Euclidean space E=Rd is generally understood by the equation:

$$A \ominus B = \{z \varepsilon E | Bz \subset A\}$$

where Bz is the translation of B by the vector Z, i.e.:

$$Bz = \{b + z | b \varepsilon B\}, \forall z \varepsilon E.$$

When the structuring element B such as a square or disc has a center located on the origin E, the erosion of A by B can be understood as the locus of points reached by the center of B when B moves inside A.

The erosion of A by B is also given by the expression:

$$A \ominus B = \cap_{b \varepsilon B} A_{-b}.$$

The dilation of A by the structuring element B is defined by:

$$A \oplus B = \cup_{b \varepsilon B} A_b.$$

The dilation is commutative, also given by:

$$A \oplus B = B \oplus A = \cup_{a \varepsilon A} B_a.$$

As before, when the structuring element B such as a square or disc has a center located on the origin E, the dilation of A by B can be understood as the locus of the points covered when the center of B moves inside A.

Figure 8:
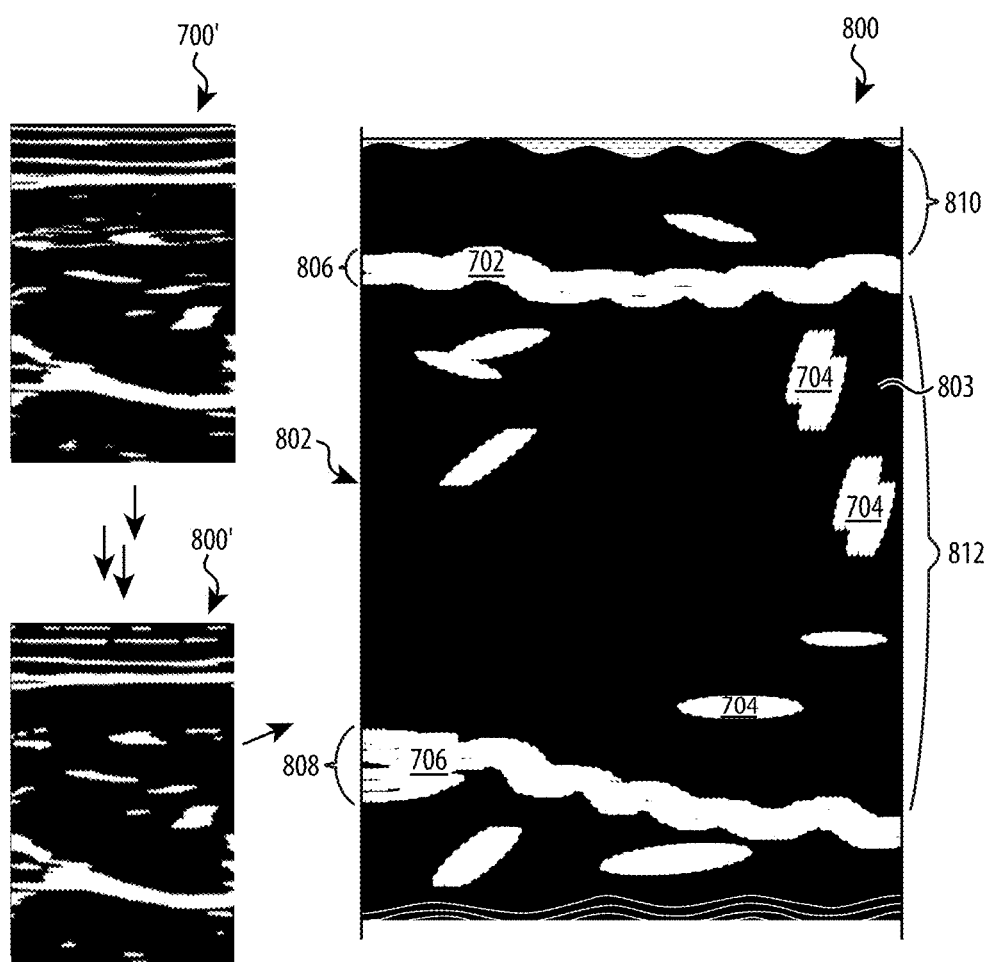
FIG. 8 depicts a conceptual illustration of a morphed image provided from the image in accordance with at least one embodiment.

More simply sated, for at least one embodiment the morphological function of opening is applied so as to further reduce the number of non-confirmed "white" elements within the binary image 700 so as to result in a reduced element image shown as morphed image 800, shown in FIG. 8. Again conceptual morphed image 800 corresponds generally to actual morphed image 800'.

Comparing morphed image 800 to binary image 700 it can and will be seen that the majority of smaller white elements, such as element 708 shown in FIG. 7, have been removed by the morphing process in providing morphed image 800. This provides the removal of larger undefined white objects that may reduce confidence in the results.

With the elements of the processed binary image now further reduced it is quite clear that this morphed image 800 is distantly related to original scan image 200. However, because of the binary nature of morphed image 800 and the reduced number of elements, morphed image 800 is advantageously poised to permit the identification and distinguishing of a black and white element 802 within the morphed image 800, block 410.

As the scan image is known to have a scale, a determination of the area for the distinguished muscle tissue 812 is now permitted with a high degree of precision using the thickness 902A, the cross-sectional area determinable from the thickness 902A and width 902B, and so on, block 412. Having the correct thickness allows for more accurate black and white pixel identification.

For example, a single thickness 902A measured at a single point across the distinguished muscle tissue 812 may be used to determine the muscle tissue ratio of contractile to non-contractile tissue. It may be assumed that the single thickness 902A allows for an adequately accurate determination of muscle tissue quality or intramuscular fat content.

However, in other examples, a number of thicknesses 902A measured at various points across the distinguished muscle tissue 812 may be used to determine the muscle tissue quality. In some implementations, these multiple thicknesses 902A may be averaged to determine the muscle tissue quality. Such averaging may use the mean, median, mode, midrange value, and so on. This may provide a more accurate determination of muscle tissue quality than measuring at only a single point. Increased accuracy may be achieved by considering an increasing number of thicknesses 902A.

In various other examples, the cross-sectional area of the muscle tissue 812 may be used to determine the muscle tissue quality. The cross-sectional area may be determined by multiplying the thickness 902A by the width 902B. In some implementations, a more accurate cross-sectional area of the muscle tissue quality may be determined by multiplying multiple thicknesses 902A measured at multiple points by multiple widths 902B measured at multiple points.

A scan may include only a portion of a muscle tissue 812. As such, in some implementations, data regarding the muscle tissue determined from a scan may be correlated to tissue models in order to estimate the quality or fat content of the entire muscle tissue, including both the portion within the scan and the portion not within the scan. In this way, a more accurate determination of muscle tissue quality may be obtained.

Additionally, data determined from multiple scans may be combined. For example, multiple scans may each include a portion of a muscle tissue 812. As such, the muscle tissue 812 quality and fat content determined using each scan may be combined in order to determine a total muscle tissue quality and/or fat content.

Although refinement 450 is illustrated and described as distinguishing the muscle tissue 812 by identifying the generally horizontal and horizontally continuous bands 806, 808 and determining the tissue in the middle, it is understood that this is an example. In other implementations, other methods may be used to distinguish the muscle tissue without departing from the scope of the present disclosure.

For example, with reference again to FIG. 8, the muscle tissue 812 will be the largest element composed of contiguous pixels of black value in the morphed image 800. Thus, in this example, the largest element composed of continuous black and white pixels in the morphed image 800 may be found and identified to distinguish the muscle tissue 812, regardless of any presence of determination of generally horizontal and horizontally continuous bands 806, 808. A ratio of the black to white pixels provides a rough index of the muscle tissue quality between horizontally continuous bands 806, 808.

By way of another example, three main layers may be identified from the morphed image 800. These may correspond to the body fat tissue 810, the muscle tissue 812, and the tissue below the muscle tissue 812 (such as bone, other muscle tissues, and so on). These three tissues may be separated by the generally horizontal and horizontally continuous bands 806, 808. Since it may be known that the muscle tissue 812 will be the middle layer, the three main layers may be identified from the morphed image 800 and the muscle tissue 812 distinguished based on its position in the three main layers. A determination of black area to white area would then be evaluated on the muscle tissue 812 to determine a muscle quality measurement.

To briefly summarize, for at least one embodiment, the method of non-invasive determination of human muscle tissue quality includes receiving at least one ultrasound scan image (block 302) of at least a portion of a skin layer as disposed above one or more additional tissue layers, the skin layer defining a horizontal axis and the image provided by a plurality of pixels; blurring the pixels of the image (block 404); thresholding the pixels of the image to provide an image having a plurality of structural elements of different sizes and setting the elements as black (contractile) or white (fat, scar and connective tissue) (block 406); morphing the structural elements of the binary image to remove small structural elements and connect large structural elements (block 408); distinguishing contractile muscle tissue from remaining structural elements (block 410); and determining the muscle tissue quality (block 412).

Figure 9:
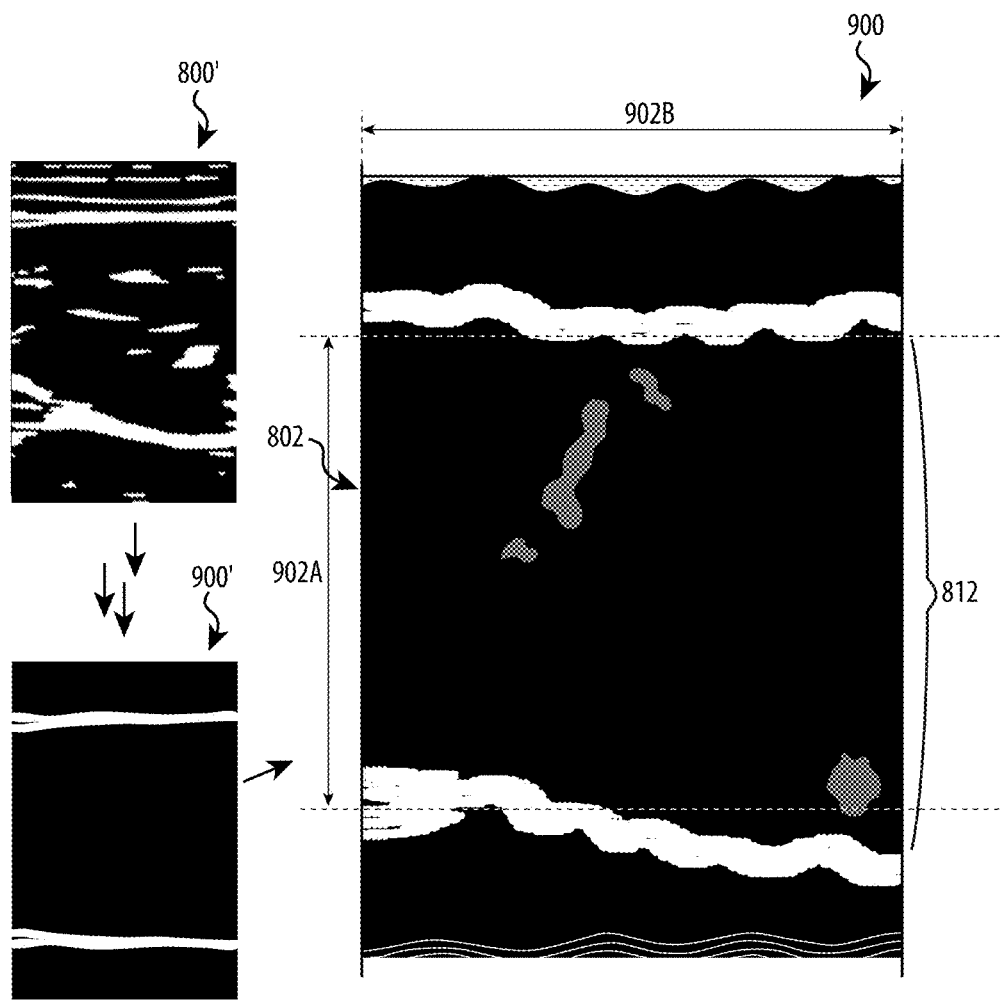
FIG. 9 depicts a conceptual illustration of the resulting processed image for non-invasive determination of human muscle tissue size in accordance with at least one embodiment.
Figure 10:
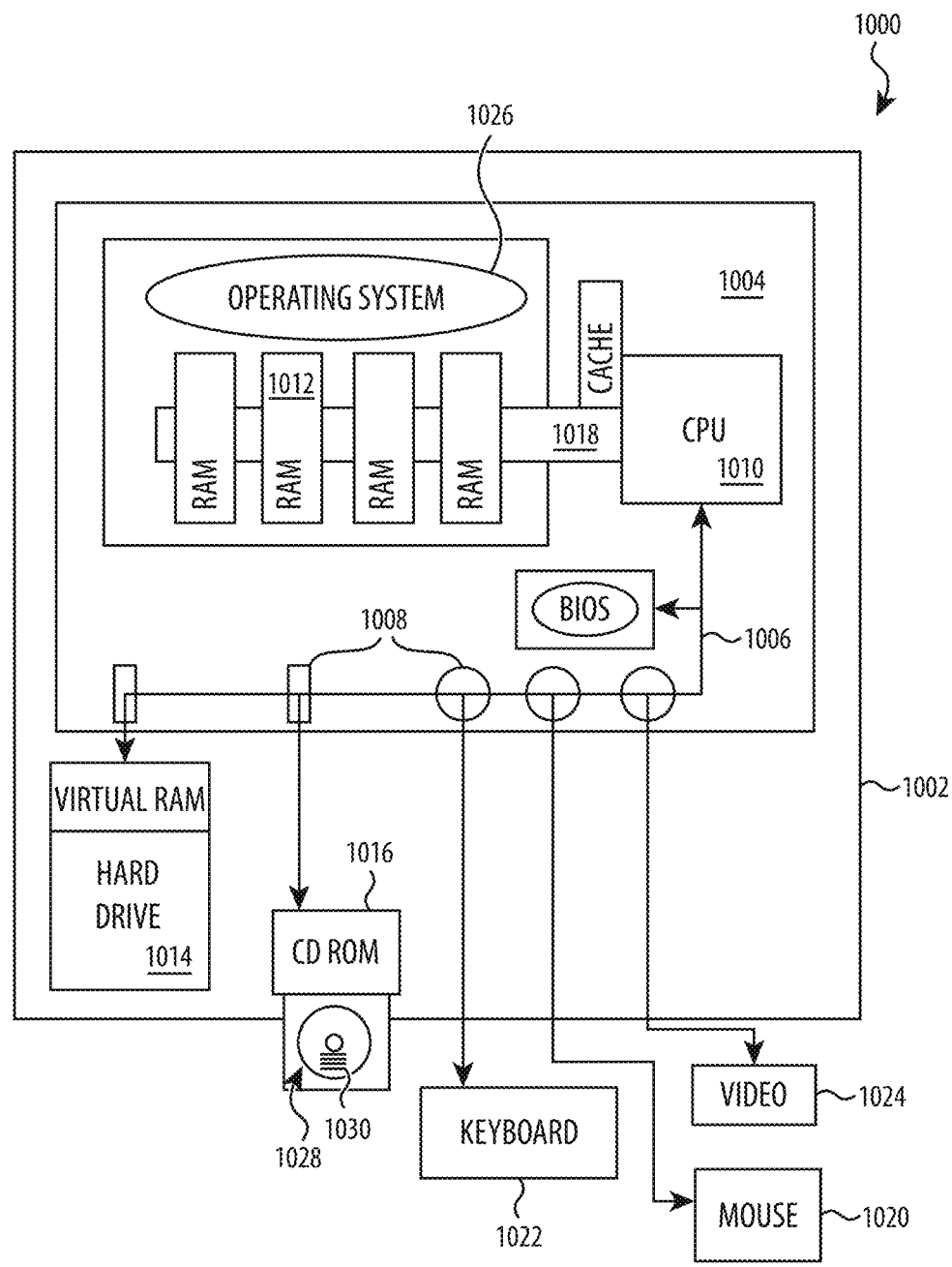
FIG. 10 depicts a block diagram of a computer system in accordance with at least one embodiment.

With the muscle tissue quality now determined, method 400 may return the determined muscle tissue quality to the operator, block 416. Various information based upon the determined muscle tissue quality may also be returned to the operator.

Where intramuscular fat is determined, the thresholding the pixels of the image provides black (contractile tissue), gray (non-contractile fat tissue) and white (non-contractile and non-fat tissue). Morphing of the structural elements and distinguishing intramuscular fat content are then determined based on the use of the gray pixel number. As shown in FIG. 9, an illustrative morphed image for intramuscular fat is shown where the black pixels have been previously threshold into black, gray and white based on the difference of impedance between the non-contractile fat and non-contractile non-fat components. As in the previous embodiments, the black pixels represent the contractile muscle fibers.

A muscle tissue quality rating may also be returned to the operator. In some implementations, the muscle tissue quality rating may involve a scale, such as a rating between "unfit" quality and "fit" quality, a value between 1 and 100, and so on. The muscle tissue quality rating may be based on comparison of muscle tissue qualities previously measured, or a historical muscle tissue quality (such as where analysis is repeated over time upon additional scan images to evaluate the muscle tissue quality over time), comparison to other subjects (such as subjects with similar characteristics like age, gender, occupation, sport, and so on), comparison to one or more muscle tissue quality goals (such as a performance objective to increase muscle tissue quality, reduce scarring in an injured muscle, make a muscle sleeker, and so on), comparison to a similar muscle over time and with age, and so on. Any of this data to which the muscle tissue quality may be compared may be retrieved from one or more storage medium in order for the comparison to be performed. The muscle tissue quality findings may also be combined with strength and power numbers for the muscle to have a measure of the strength of the muscle per unit of mass. Strength and power could be determined as is well known in the art, for example, by weight lifting, speed testing, agility testing and the like.

Further, intramuscular fat content may also be used to indicate that the subject may be overweight or be given a value of between 1 and 100, for example. Intramuscular fat content may also be used to prognosticate the potential development of a disease state or the likely presence of a disease state. For example, a intramuscular fat content of 25% may be indicative of glucose intolerance and request the operator to perform additional confirmatory tests on the subject.

By way of another example, advice based on the muscle tissue quality may also be returned to the operator. In some implementations, advice regarding training, food, and/or other parameters may be based on comparison of the muscle tissue quality to a desired muscle tissue quality or muscle tissue quality goal. For example, advice regarding performance of specific exercises, additional weight or repetitions, increased or decreased protein, increased or decreased carbohydrates, and so on may be returned when the muscle tissue quality is below the desired muscle tissue quality or muscle tissue quality goal, above the desired muscle tissue quality or muscle tissue quality goal, and so on. Specific advice to return based on the results of a comparison, as well as the comparison results under which to return such advice, may be retrieved from one or more storage medium.

The determination of muscle tissue quality as provided by SNTA 100 and/or methods 300, 350 and 400 is applicable in a wide variety of qualified formulas for the determination of a number of different values which may be used by the subject or subject's doctor, trainer, caretaker, or other in a variety of different ways.

For example, a baseball trainer may utilize the above to determine the muscle tissue quality to evaluate muscle tissue quality of a batter who is attempting to increase muscle quality to be able to hit further or run faster. The advice returned may compare the batter's muscle tissue quality against previous determinations and/or other batters in the field, as well as indicate an adjusted training plan for the batter to maximize continued muscle fitness towards the batter's goal.

In yet another example, a medical professional may utilize the above to determine muscle tissue quality of a patient who has been injured in order to determine whether it is safe for the patient to increase his or her exercise routine. Muscle tissues may scar or become infiltrated with fat tissue while a patient is injured, and the patient may re-injure the muscle anew if they attempt to exercise while the muscle quality is low. As such, the advice may indicate whether or not the patient's muscle tissue quality has sufficiently increased to the point that it is safe for the patient to resume exercise.

In still another example, a trainer may utilize the above to determine muscle tissue fitness and appearance of a body builder. The advice may indicate that the body builder is increasing muscle quality for certain muscles but not for other muscles. The trainer may use the information to focus fitness on the muscle groups that have need of an increase in muscle quality. Further, the trainer may determine that certain types of exercise for that body builder lead to a leaner and more sculpted look than other exercises, i.e., provide a higher quality muscle.

In yet another example, an physician may utilize the above to follow an aging patient's muscle quality as an indicator of overall mobility and potential health concerns. An aging patient may show decreased muscle quality and indicate to the physician that the patient requires additional exercise, diet modification, medications, or other like advice. Continued analysis of the patients muscle quality can be used to vary parameters to increase the patient's overall mobility and health. A physician may compare the muscle tissue quality to a muscle tissue quality goal, or compare the intramuscular fat content to an intramuscular fat goal. Furthermore, a physician may measure muscle tissue quality and/or intramuscular fat over time and compare an intramuscular fat to an intramuscular fat goal that is based on a historic quality, and/or based on intramuscular fat qualities of other subjects.

In still yet another example, an physician may utilize a patient's intramuscular fat content to identify risk factors for the subject related to being overweight, having glucose intolerance and possibly diabetes, having dyslipidemia, having an increased risk of cardiovascular disease and the like. The physician may take corrective action like modifying the patient's diet or exercise regiment, providing the patient with medications, and the like. The patient can be followed and re-tested over time to correlate the effectiveness of the corrective action to the patient's intramuscular fat. In some cases, the physician may test two or more, three or more, four of more, five or more, six or more, or seven or more muscles for intramuscular fat and take an average content score.

With respect to the above description of SNTA 100 and methods 300, 350 and 400, it is understood and appreciated that the method may be rendered in a variety of different forms of code and instruction as may be preferred for different computer systems and environments. To expand upon the initial suggestion of a processor based device such as a computer 114 shown in FIG. 1 and discussed above, FIG. 10 is a high-level block diagram of an example computer system 1000. Computer system 1000 has a case 1002, enclosing a main board 1004. The main board 1004 has a system bus 1006, connection ports 1008, a processing unit, such as Central Processing Unit (CPU) 1010 with at least one processor/microprocessor (not shown) and a memory storage device, such as main memory 1012, and optionally a solid state drive or hard drive 1014 and/or CD/DVD ROM drive 1016.

Memory bus 1018 couples main memory 1012 to CPU 1010. A system bus 1006 couples storage devices such as, but not limited to, hard drive 1014, CD/DVD ROM drive 1016 and connection ports 1008 to CPU 1010. Multiple input devices may be provided, such as for example a mouse 1020 and/or keyboard 1022. Multiple output devices may also be provided, such as for example a video display 1024 and a printer (not shown). In varying embodiments, the video display 1024 may also be a touch sensitive input device.

Computer system 1000 may be a commercially available system, such as a desktop workstation unit provided by IBM, Dell Computers, Gateway, Apple, Sun Microsystems, or other computer system provider. Computer system 1000 may also be a smart phone or tablet computer such as an iPhone or iPad provided by Apple, the HP Slate, the Augen or Archos Android tablets, the Motorola Xoom or other such device. Computer system 1000 may also be a networked computer system, wherein memory storage components such as hard drive 1014, additional CPUs 1010 and output devices such as printers are provided by physically separate computer systems commonly connected together in the network. Those skilled in the art will understand and appreciate that physical composition of components and component interconnections comprising computer system 1000, and select a computer system 1200 suitable for the schedules to be established and maintained.

When computer system 1000 is activated, an operating system 1026 may load into main memory 1012 as part of the boot strap startup sequence and ready the computer system 1000 for operation. At the simplest level, and in the most general sense, the tasks of an operating system may fall into specific categories—process management, device management (including application and user interface management) and memory management.

In such a computer system 1000, the CPU 1010 may be operable to perform one or more of the methods of non-invasive determination of muscle tissue quality as described above. Those skilled in the art will understand that a computer-readable medium 1028 on which is a computer program 1030 for non-invasive determination of muscle tissue quality may be provided to the computer system 1000. The form of the medium 1028 and language of the program 1030 are understood to be appropriate for computer system 1000. Utilizing the memory stores, such as for example one or more hard drives 1014 and main memory 1012, the operable CPU 1010 will read the instructions provided by the computer program 1030 and operate to perform as SNTA 100 as described above.

To summarize, for at least one embodiment, a non-invasive system of determining muscle tissue quality and/or intramuscular fat content is provided by a processing unit; a memory storage device coupled to the processing unit; the processing unit being adapted to: receive at least one ultrasound scan image of at least a portion of a skin layer as disposed above one or more additional tissue layers, the skin layer defining a horizontal axis and the image provided by a plurality of pixels; blurring the pixels of the image; threshold the pixels of the image to provide an image having a plurality of structural elements of different sizes and gray scale; morph the structural elements of the binary image to remove small structural elements and connect large structural elements; distinguish a ratio of contractile muscle tissue from non-contractile tissue; and determine the muscle tissue quality. Where intramuscular fat context in required, the non-contractile tissue is further distinguished into fat and non-fat tissue.

Figure 11:
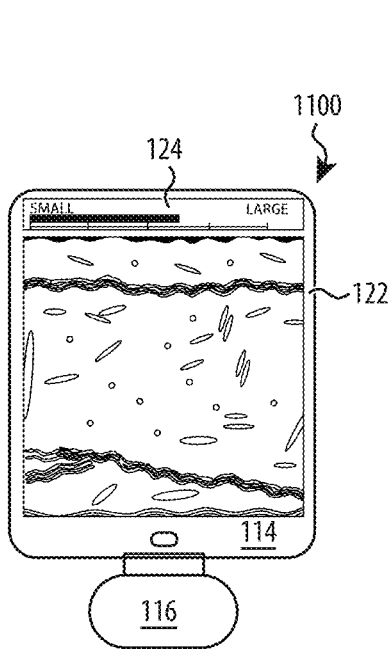
FIG. 11 depicts a conceptual illustration of a first alternative configuration for a system for non-invasive tissue evaluation that may be used to determine human muscle tissue quality and/or fat content in accordance with at least one embodiment.

With respect to the various forms of the processor based device, such as the computer 114, further discussed and described as computer system 1000, FIGS. 11-16 present alternative embodiments for the structural arrangement of components comprising SNTA 100. More specifically, for alternative SNTA 1100 as shown in FIG. 11, the ultrasound transducer 116 is coupled directly to the computer 114, such that SNTA 1100 is itself disposed adjacent to the target tissue 108 (not shown).

Figure 12:
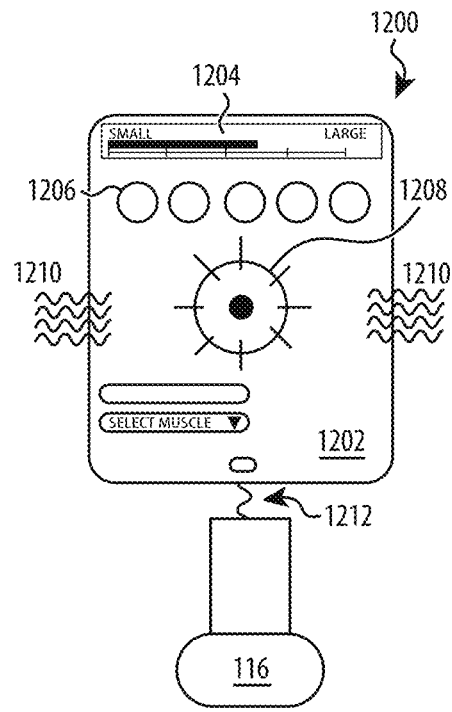
FIG. 12 depicts a conceptual illustration of a second alternative configuration for a system for non-invasive tissue evaluation that may be used to determine human muscle tissue quality and/or fat content in accordance with at least one embodiment.
Figure 13:
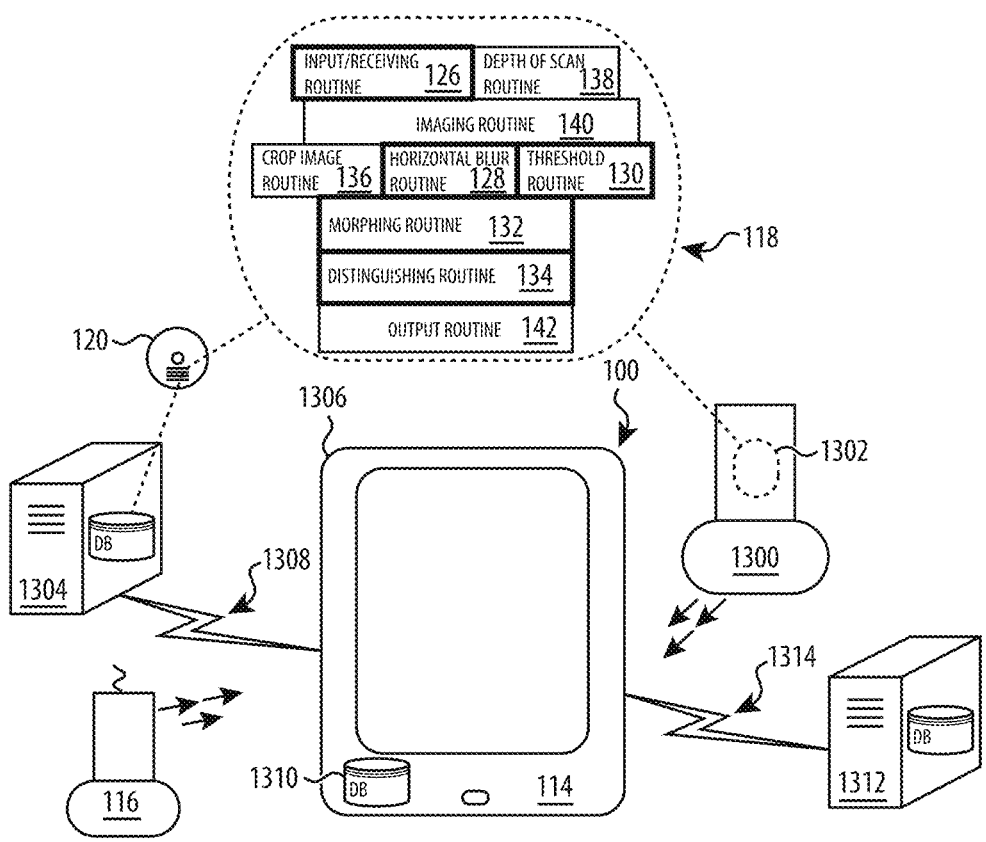
FIG. 13 depicts a conceptual illustration of a third alternative configuration for a system for non-invasive tissue evaluation that may be used to determine human muscle tissue quality and/or fat content in accordance with at least one embodiment.

For alternative SNTA 1200 shown as FIG. 12, a dedicated processor based device such as a customized computer 1202 is provided, as opposed to adapting a pre-existing smart phone, tablet computer or other computer system. For SNTA 1200, the display 122 of SNTA 1200 is not shown so as to illustrate that alternative output devices such as an indicator 1204, lights 1206, speaker 1208, vibrator 1210 and/or combinations thereof can provide an operator with an indication of the non-invasively determined muscle tissue quality. As with SNTA 1100, the ultrasound transducer 116 may be directly coupled to the customized computer 1202, or tethered by a communications link 1212—wireless or wired as shown.

Further, for yet other embodiments, the computer program 118 to adapt a computer 114 may be provided directly by enhanced ultrasound transducer 1300. More specifically, the computer program 118 may be incorporated as part of the circuit structure 1302 of enhanced ultrasound transducer 1300 such that upon connection to the computer 114, SNTA 100 is provided.

As suggested above with respect to FIG. 1, the computer program 118 may also be provided by a non-portable media such as a disc 120 to a third party computer, such as computer 1304, providing an application platform such as but not limited to the Apple App Store. A user can then connect his or her computer 114, such as tablet computer 1306 to the third party computer 1304 by a network 1308 (wired or wireless) or other communication channel and obtain computer program 118 so as to adapt his or her computer 1306 to perform as SNTA 100 when a scan of a target muscle is provided.

In varying embodiments, this scan may be provided by coupling computer 1306 to ultrasound transducer 116 operated as described above, receiving a scan of a target muscle from internal storage 1310, or receiving a scan of a target muscle from another computer system 1312 via wired or wireless network 1314, or other appropriate communication channel.

Figure 14:
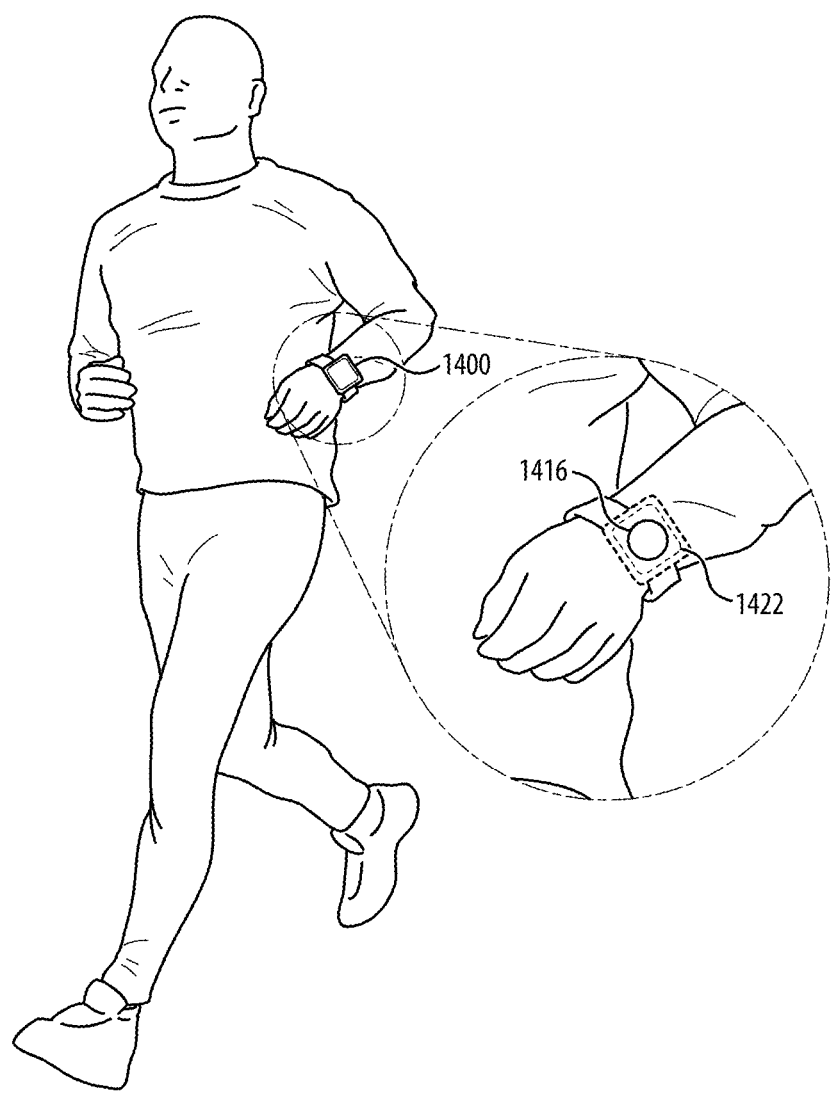
FIG. 14 depicts a conceptual illustration of a fourth alternative configuration for a system for non-invasive tissue evaluation that may be used to determine human muscle tissue quality and/or fat content in accordance with at least one embodiment.

As shown in FIG. 14, in some embodiments, the SNTA 1400 may be a wearable device, such as a smart watch or other device operable to couple around a user's body part. The SNTA 1400 may include a transducer 1416 positioned adjacent the user in order to obtain scans and/or other data at a variety of different times, such as during a user's workout. The SNTA 1400 may also include a display 1422 for providing real time and/or other analysis information to the user.

Figure 15:
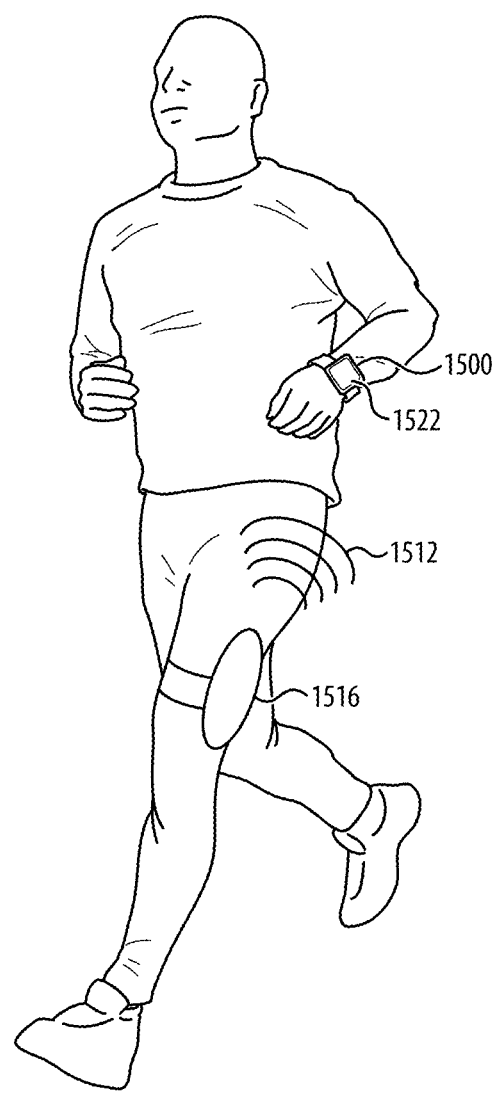
FIG. 15 depicts a conceptual illustration of a fifth alternative configuration for a system for non-invasive determination of human muscle tissue quality and/or fat content in accordance with at least one embodiment.

As shown in FIG. 15, in other embodiments, a wearable SNTA 1500 may be used with a separately wearable transducer 1516. In this way, the SNTA 1500 may be coupled around one body part while the transducer 1516 obtains one or more scans related to tissues located in another body part. The SNTA 1500 may receive data regarding such scans from the transducer 1516, such as wirelessly 1512, and provide real time and/or other analysis information to the user via a display 1522.

Figure 16:
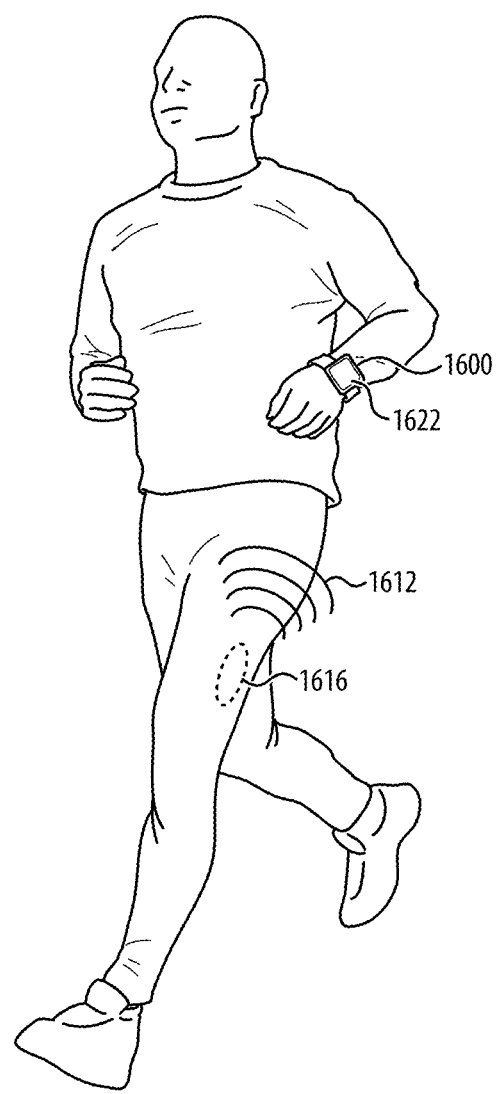
FIG. 16 depicts a conceptual illustration of a sixth alternative configuration for a system for non-invasive determination of human muscle tissue quality and/or fat content in accordance with at least one embodiment.

As shown in FIG. 16, in still other embodiments, a wearable SNTA 1600 may be used with a transducer implant 1616 located inside the user's body. In this way, the SNTA 1600 may obtain one or more scans related to tissues located in the body without requiring attachment and positioning of a transducer for use. The SNTA 1600 may receive data regarding such scans from the transducer implant 1616, such as wirelessly 1612, and provide real time and/or other analysis information to the user via a display 1622.

To summarize, for at least one embodiment, the present disclosure is provided upon a non-transitory machine readable medium on which is stored a computer program comprising instructions to adapt a computer system having a processor to permit non-invasive determination of human muscle tissue quality and/or intramuscular body fat percent. This computer program includes computer executable instructions to provide a receiving routine operatively associated with an input device for receiving at least one ultrasound scan image of at least a portion of a skin layer as disposed above one or more additional tissue layers, the skin layer defining a horizontal axis and the image provided by a plurality of pixels; a blurring routine, in this case for horizontally blurring the pixels of the image; a thresholding routine for thresholding the pixels of the image to provide a binary image having a plurality of structural elements of different sizes and of different gray scale; an optional morphing routine for morphing the structural elements of the binary image to remove small structural elements and connect large structural elements; and a distinguishing routine for distinguishing muscle tissue from remaining structural elements and determining the muscle tissue quality and/or the intramuscular fat content. This computer program may optionally compare the muscle tissue quality to a muscle tissue quality goal, or compare the intramuscular fat content to an intramuscular fat goal. Furthermore, this computer program may optionally compare an intramuscular fat to an intramuscular fat goal that is based on a historic quality, and/or based on intramuscular fat qualities of other subjects.

Changes may be made in the above methods, systems and structures without departing from the scope hereof. It should thus be noted that the matter contained in the above description and/or shown in the accompanying drawings should be interpreted as illustrative and not in a limiting sense. The following claims are intended to cover all generic and specific features described herein, as well as all statements of the scope of the present method, system and structure, which, as a matter of language, might be said to fall therebetween.

In the present disclosure, the methods disclosed may be implemented as sets of instructions or software readable by a device. Further, it is understood that the specific order or hierarchy of steps in the methods disclosed are examples of sample approaches. In other embodiments, the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a non-transitory machine-readable medium having stored thereon instructions, which may be used to program a computer system (or other electronic devices) to perform a process according to the present disclosure. A non-transitory machine-readable medium includes any mechanism for storing information in a form (e.g., software, processing application) readable by a machine (e.g., a computer). The non-transitory machine-readable medium may take the form of, but is not limited to, a magnetic storage medium (e.g., floppy diskette, video cassette, and so on); optical storage medium (e.g., CD-ROM); magneto-optical storage medium; read only memory (ROM); random access memory (RAM); erasable programmable memory (e.g., EPROM and EEPROM); flash memory; and so on.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. A non-invasive method of determining human muscle tissue quality, comprising:
receiving at least one ultrasound scan image of at least a portion of a skin layer as disposed above one or more additional tissue layers, the skin layer defining a horizontal axis and the ultrasound scan image provided by a plurality of black, gray, and white pixels;
blurring the plurality of black, gray, and white pixels of the ultrasound scan image;
thresholding the plurality of blurred black, gray, and white pixels of the ultrasound scan image to provide a binary image having a plurality of elements, set the elements being black elements or white elements;

morphing the elements of the binary image to produce a morphed binary image, by:
  removing first structural elements having a first size below a threshold; and
  connecting second structural elements having a second size above the threshold;
distinguishing muscle tissue; and
determining a human muscle tissue quality by evaluating a ratio of black to white pixels; wherein:
the morphed binary image comprises:
  a topmost band of contiguous white pixels extending across the morphed binary image;
  a middle band of contiguous black pixels extending across the morphed binary image and adjacent the topmost band; and
  a bottom band of contiguous white pixels extending across the morphed binary image and adjacent the middle band of contiguous black pixels;
  the topmost, middle, and bottom bands extend continuously from a first side of the morphed binary image to a second side of the morphed binary image;
  muscle tissue corresponds to the middle band in the morphed binary image.

2. The method of claim 1, wherein distinguishing the muscle tissue further includes evaluating at least a subset of remaining elements.

3. The method of claim 2, wherein evaluating at least a subset of the remaining elements includes determining, for each element, one or more characteristics selected from a group consisting of: area, center of mass, and horizontal length.

4. The method of claim 1, further comprising imaging a selected portion of a subject's body with an ultrasound device having a movable transducer to provide the ultrasound scan image.

5. The method of claim 4, wherein the determining of human muscle tissue quality is performed about contemporaneously with the imaging of the subject with the ultrasound device for another purpose.

6. The method of claim 1, wherein the method is repeated over time upon additional ultrasound scan images to evaluate the muscle tissue quality over time.

7. A non-invasive method of determining human muscle tissue quality, comprising:
  providing an ultrasound device having a movable transducer, the transducer configured to operate in a high frequency range;
  selecting a target area of a subject;
  adjusting the ultrasound device for a depth of scan appropriate for a selected target area;
  disposing the transducer proximate to the subject and perpendicular to the selected target area;
  scanning the selected target area by processing ultrasound reflection received by the transducer to provide at least a partial scan image of the selected target area, the partial scan image provided by a plurality of pixels;
  blurring the pixels of the partial scan image;
  thresholding the blurred pixels of the partial scan image to provide a binary image having a plurality of black and white elements;
  morphing the elements of the binary image with morphological functions to produce a morphed binary image, the morphological functions comprising:
    removing white holes from the black elements; and
    removing black holes from the white elements;
  distinguishing muscle tissue with a distinguishing routine;
  evaluating a ratio of black pixels within the black elements to white pixels within the white elements; and
  determining a human muscle tissue quality; wherein:
    the morphed binary image comprises a continuous black band of contiguous black pixels extending across the morphed binary image between upper and lower continuous white boundaries formed of contiguous white pixels; and
    the muscle tissue corresponds to a middle black band between the upper and lower continuous white boundaries.

8. The method of claim 7, wherein the morphing is mathematical morphology.

9. The method of claim 8, wherein the morphing includes applying a morphological function for opening.

10. The method of claim 7, further comprising vertically cropping one or both sides of the partial scan image before blurring a remaining central portion of the partial scan image.

11. The method of claim 10, wherein between $1/10$ and $1/5$ of the partial scan image is vertically cropped from one or both sides.

12. The method of claim 7, wherein the method is performed in about real time.

13. The method of claim 7, wherein the method is contemporaneously performed on different partial scan images from different locations of a subject's body.

14. A non-invasive method of determining intramuscular fat of a muscle, comprising:
  receiving at least one ultrasound scan image of at least a portion of a skin layer as disposed above one or more additional tissue layers, the skin layer defining a horizontal axis and the ultrasound scan image provided by a plurality of black, gray, and white pixels;
  blurring the plurality of black, gray, and white pixels of the ultrasound scan image;
  thresholding the plurality of black, gray, and white pixels of the ultrasound scan image to provide a binary image having a plurality of black pixels and white pixels;
  morphing the pixels of the binary image to remove small structural elements and connect large structural elements, thereby producing a morphed binary image having a band of contiguous black pixels positioned between two bands of contiguous white pixels;
  distinguishing muscle tissue from fat tissue by identifying:
    the muscle tissue as a first element composed of the band of contiguous black pixels having a first range of values and extending across an entirety of the morphed binary image; and
    the fat tissue as a second element composed of the two bands of contiguous white pixels having a second range of values, each of the two bands of contiguous white pixels extending across an entirety of the morphed binary image; and
  determining the intramuscular fat content of the muscle tissue by evaluating a ratio of black to white pixels.

15. The method of claim 14, further comprising reporting the intramuscular fat of the muscle tissue.

16. The method of claim 15, further comprising comparing the intramuscular fat to an intramuscular fat goal.

17. The method of claim 16, wherein the intramuscular fat goal is based on a historic quality.

18. The method of claim 17, wherein the intramuscular fat goal is based on intramuscular fat qualities of other subjects.

19. A non-invasive method of determining a muscle tissue quality, comprising:

receiving at least one ultrasound scan image via an input/receiving routine operates to receive an ultrasound scan image of at least a portion of a skin layer as disposed above one or more additional tissue layers, the skin layer defining a horizontal axis and the ultrasound scan image provided by a plurality of black, gray, and white pixels;

blurring the plurality of black, gray, and white pixels of the ultrasound scan image via a blurring routine operates to horizontally blur the pixels of the ultrasound scan image;

thresholding the plurality of blurred black, blurred gray, and blurred white pixels of the ultrasound scan image via a thresholding routine operates to provide a binary image having a plurality of elements, set the elements being black elements or white elements;

morphing the elements of the binary image via a morphing routine operates to produce a morphed binary image, by:
  removing structural elements having a size below a threshold; and
  connecting large structural elements;

distinguishing muscle tissue via a distinguishing routine operates to:
  distinguish muscle tissue; and
  determine percent intramuscular fat;

determining a muscle tissue quality via a routine operates to evaluate a ratio of black to white pixels; and outputting one or more of a muscle tissue quality or the percent intramuscular fat via an outputting routine operates to output one or more of the muscle tissue quality or the percent intramuscular fat, wherein:

the morphed binary image comprises:

an upper band of contiguous white pixels extending across an entirety of the morphed binary image;

a middle band of contiguous black pixels adjacent the upper band and extending across an entirety of the morphed binary image; and a bottom band of contiguous white pixels adjacent the middle band and extending across an entirety of the morphed binary image;

the upper, middle, and bottom bands extend continuously from a first side of the morphed binary image to a second side of the morphed binary image; and muscle tissue corresponds to the middle band in the morphed binary image.

* * * * *